United States Patent
Butlin et al.

(10) Patent No.: US 6,552,225 B1
(45) Date of Patent: Apr. 22, 2003

(54) CHEMICAL COMPOUNDS

(75) Inventors: Roger John Butlin, Macclesfield (GB); Janet Elizabeth Pease, Macclesfield (GB); Michael Howard Block, Macclesfield (GB); Thorsten Nowak, Macclesfield (GB); Jeremy Nicholas Burrows, Macclesfield (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/069,880
(22) PCT Filed: Aug. 30, 2000
(86) PCT No.: PCT/GB00/03303
§ 371 (c)(1),
(2), (4) Date: Jun. 17, 2002
(87) PCT Pub. No.: WO01/17955
PCT Pub. Date: Mar. 15, 2001

(30) Foreign Application Priority Data

Sep. 4, 1999 (GB) .............................. 9920817
Dec. 18, 1999 (GB) .............................. 9929834

(51) Int. Cl.$^7$ ...................... A61K 31/40; A61K 31/44; A61K 31/445; A61K 31/535
(52) U.S. Cl. ...................... 564/80; 514/238.8; 514/327; 514/352; 514/425; 514/604; 544/159; 546/220; 546/305; 548/542; 564/86; 564/87
(58) Field of Search ............... 514/238.8, 327, 514/352, 425, 603, 604; 544/159; 546/220, 305; 548/542; 564/86, 87

(56) References Cited

U.S. PATENT DOCUMENTS

| | | | |
|---|---|---|---|
| 4,537,618 A | 8/1985 | Schurter et al. | 544/321 |
| 5,248,693 A | 9/1993 | Gerspacher et al. | 548/511 |
| 5,446,065 A * | 8/1995 | Witte et al. | 514/604 |
| 5,486,515 A | 1/1996 | Brown et al. | 514/229.8 |
| 5,510,386 A | 4/1996 | Empfield et al. | 546/89 |

FOREIGN PATENT DOCUMENTS

| | | |
|---|---|---|
| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 | 1/1993 |
| EP | 0 617 010 | 9/1994 |
| EP | 0 625 516 | 11/1994 |
| EP | 0625516 A | 11/1994 |
| GB | 2 278 054 | 11/1994 |
| WO | WO 93/10094 | 5/1993 |
| WO | WO 93/23358 | 5/1993 |
| WO | WO 94/26739 | 11/1994 |
| WO | WO 96/28151 | 9/1996 |
| WO | WO 97/38124 | 10/1997 |
| WO | Wo 99/44618 | 9/1999 |
| WO | WO 99/47508 | 9/1999 |
| WO | WO 99/62506 | 12/1999 |
| WO | WO 99/62873 | 12/1999 |

OTHER PUBLICATIONS

Aicher et al., "(R)–3,3,3–trifluoro–2–hydroxy–2–methylpropionamides are orally active inhibitors of pyruvate dehydrogenase kinase", Journal of Medicinal Chemistry, American Chemical Society, vol. 42, No. 15, Jul. 1999, pp. 2741–2746, XP002122777.

Aicher et al., "Secondary Amides of (R)–3,3,3–Trifluoro–2–hydroxy–2–methylpropionic Acid as Inhibitors of Pyruvate Dehydrogenase Kinase", J. Med. Chem., 2000, vol. 43, No. 2, pp. 236–249.

Bayles et al., "A Smiles Rearrangement Involving Non–Activated Aromatic Systems; the Facile Conversion of Phenols to Anilines", Synthesis, 1977, vol. 1. pp. 33–34.

Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp, 31–33.

Bebernitz et al., "Anilides of (R)–Trifluoro–2–hydroxy–2–methylpropionic Acid as Inhibitors of Pyruvate Dehydrogenase Kinase", J. Med. Chem., 2000, vol. 43, No. 11, pp. 2257–2266.

Empfield et al., "4–sulfonamidoanilide Tertiary Carbinols: A Novel Series Of Potassium Channel Openers", Bioorg Med. Chem. Letters, 1997, vol. 7, No. 7, pp. 775–778, XP004136128 see table I, compounds e, f.

Fenwick, "The Synthesis of 2,2–Bis(Trifluoromethyl)Benzopyran Derivatives: A New Route to an Import Class of Postassium Channel Activators", Tetrahedron Letters, vol. 34, No. 11, 1993, pp. 1993.

(List continued on next page.)

Primary Examiner—Peter O'Sullivan
(74) Attorney, Agent, or Firm—Morgan, Lewis & Bockius LLP

(57) ABSTRACT

A compound of formula (I) wherein: $R^1$, $R^2$, $R^3$, $R^4$, $R^5$, $R^6$ and $R^7$ are as defined within; or a pharmaceutically acceptable salt or an in vivo hydrolysable ester thereof is described. The use of compounds of formula (I) in the production of an elevation of PDH activity in a warm-blooded animal such as a human being are also described. Pharmaceutical compositions, methods and processes for preparation of compounds of formula (I) are detailed.

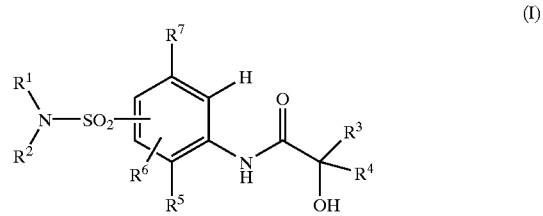

(I)

13 Claims, No Drawings–

OTHER PUBLICATIONS

Furr et al., "A Novel Non–Steroidal, Peripherally Selective Antiandrogen", J. Endrocrinol., 1987, vol. 113 (3), R7–R9.

Glen et al., Structure–Activity Relationships among Non–steriodal Antiandrogens, Third SCI–RSC Medicinal Chemistry Symposium, 1986, vol. 55, pp. 345–361.

Grant et al., "Anilide Tertiary Carbinols: A New Structural Class Of Potent Potassium Channel Openers", Bioorg. Med. Chem. Lett., 1993, vol. 3 (12), pp. 2723–2724.

Howe et al., "Zeneca ZD6169: A Novel $K_{ATP}$ Channel Opener with in Vivo Selectivity for Urinary Bladder", J. Pharmacol. Exp. Ther. 1995, vol. 274 (2), pp, 884–890.

Jackman et al., "Studies in the Field of Diuretics", J. Pharm. and Pharmacol., vol. 12, 1960, pp. 648–655; Chemical Abstracts, vol. 55, No. 9, May 1, 1961, Columbus, Ohio, US; abstract No. 8336a, XP002107578 see abstract, col. 8336, lines 8–9 &.

Li et al., "Zeneca ZD6169 and Its Analogs from a Novel Series of Anilide Tertiary Carbinols: in vitro $K_{ATP}$ Channel Opening Activity in Bladder Detrusor", Pharmacology, 1995, vol. 51, pp. 33–42.

Mann et al., "Divese mechanisms of inhibition of pyruvate dehydrogenase kinase by structurally distinct inhibitors", Biochemica et Biophysica Acta, vol. 1480, 2000, pp 283–292.

Morris et al., "Hydrogen Bonding Parameters In The S.A.R. of Non–Steroidal Anti–Androgens", Pharmacol. Libr., 1987, vol. 10, pp. 204–206.

Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp, 447–455.

Ohnmacht et al., N–Aryl–3,3, 3–trifluoro–2–hydroxy–2–methylpropanamides: $K_{ATP}$ Potassium Channel Openers. Modifications on the Western Region, J. Med. Chem., 1996, vol. 39 (23), pp. 4592–4601.

Ohnmacht et al., N–Aryl–3,3, 3–trifluoro–2–hydroxy–2–methylpropanamides: $K_{ATP}$ Potassium Channel Openers. Modifications on the Western Region, J. Med. Chem., 1996, Additions and Corrections, vol. 39 (6), p. 1048.

Russell, "Crystal Receptor Models In Medicinal Chemistry: Application To The Generation of Highly Potent Potassium Channel Openers", Bioorg. Med. Chem. Lett. 1996, vol. 6 (7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Activity of ZD6169 and Its Analogs: Effect on $^{86}$Rb Efflux and $^{3}$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Antiandrogen 4'–Cyano–3–[(4–fluorophenyl)sulfonyl]–2–hydroxy–2–methyl–3'–(trifluoromethyl)– propionanilide and the Determination of the Absolute Configuration of the Active Enantiomer", J. Med. Chem. 1988. vol. 31 (4), pp. 885–887.

Wakeling et al., "Receptor Binding And Biological Activity Of Steriodal and Nonsteriodal Antiandrogens", J. Steriod Biochem., 1981, vol. 15, pp. 355–359.

* cited by examiner

CHEMICAL COMPOUNDS

This application is a 371 of PCT/GB00/03303 filed Aug. 30, 2000.

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans, in particular the treatment of diabetes mellitus, peripheral vascular disease and myocardial ischaemia in warm-blooded animals such as humans, more particularly to their use in the manufacture of medicaments for use in the treatment of diabetes mellitus in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as both non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes mellitus Zhou et al. (1996) Diabetes 45:580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischaemia and reperfusion, (Zaidan et al., 1998; J. Neurochem. 70:233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock, 24:3–18), has been shown to have the predicted effects in reducing glycaemia, (Stacpoole et al., 1978; N. Engl. J. Med. 298:526–530), and as a therapy for myocardial ischaemia (Bersin and Stacpoole 1997; American Heart Journal, 134:841–855) and lactic acidaemia, (Stacpoole et al., 1983; N. Engl. J. Med. 309:390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4:3224–3233). E1 catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication No. 625516 refers to compounds which are capable of relaxing bladder smooth muscle and which may be used in the treatment of urge incontinence. We have found, surprisingly, that compounds also containing a sulphonamide moiety disclosed in the present invention are very good at elevating PDH activity, a property nowhere disclosed in EP 625516. The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21:1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298:526–530). A compound that activates PDH may also be useful in treating Alzheimer disease (AD) (J Neural Transm (1998) 105:855–870).

Accordingly, the present invention provides a compound of formula (I):

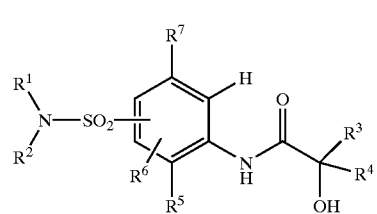

wherein:
$R^1$ and $R^2$ are each selected independently from hydrogen, phenyl optionally substituted by one or more Q, naphthyl optionally substituted by one or more Q, $C_{3-6}$cycloalkyl optionally substituted by one or more Q, $C_{2-6}$alkenyl, $C_{2-6}$alkynyl, $C_{1-6}$alkyl optionally substituted by one or more Q, $R^8T$—, $R^9C_{1-6}$alkylT— and a heterocyclic group optionally substituted on a ring carbon by one or more Q and wherein if said heterocyclic group contains an —NH— moiety that nitrogen may be optionally substituted by a group selected from D, or $R^1$ and $R^2$ together with the nitrogen atom to which they are attached form a group Het which is optionally substituted on a ring carbon by one or more Q and wherein if group Het contains an —NH— moiety that nitrogen may be optionally substituted by a group selected from D;

$R^3$ and $R^4$ are independently $C_k$alkyl optionally substituted by 1 to 2k+1 atoms selected from fluoro and chloro wherein k is 1–3;

or $R^3$ and $R^4$ together with the carbon atom to which they are attached, form a $C_m$cycloalkyl ring optionally substituted by 1 to 2m-2 fluorine atoms wherein m is 3–5;

$R^5$ is hydrogen, $C_{1-6}$alkyl, halo$C_{1-6}$alkyl, $C_{1-6}$alkoxy, halo$C_{1-6}$alkoxy, cyano, nitro, $C_{2-6}$alkenyloxy, trifluoromethylthio, halo, hydroxy, amino, N—($C_{1-6}$alkyl)amino, N—($C_{1-6}$alkyl)$_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoyl, N—($C_{1-6}$alkyl)aminosulphonyl, N—($C_{1-6}$alkyl)$_2$aminosulphonyl, carboxy, carbamoyl, N—($C_{1-6}$alkyl)carbamoyl, N—($C_{1-6}$alkyl)$_2$carbamoyl, $C_{1-6}$alkoxycarbonyl, formyl, $C_{1-6}$alkanoyl, $C_{1-6}$alkanoyloxy, $C_{2-6}$alkenyl or $C_{2-6}$alkynyl;

$R^6$ is hydrogen or Q;

$R^7$ is hydrogen, trifluoromethyl, $C_{1-4}$alkyl, halo, hydroxy, trifluoromethoxy, cyano, $C_{1-4}$alkoxy, formyl, $C_{1-4}$alkanoyl, $C_{1-4}$alkanoyloxy, amino, N—($C_{1-4}$alkyl)amino, N—($C_{1-4}$alkyl)$_2$amino, $C_{1-4}$alkanoylamino, $C_{1-4}$alkanoyl(N—$C_{1-4}$alkyl)amino, nitro, carboxy, carbamoyl, ureido, $C_{1-4}$alkoxycarbonyl, thiol, $C_{1-4}$alkylsulphanyl, $C_{1-4}$alkylsulphinyl, $C_{1-4}$alkylsulphonyl, sulphamoyl, N—($C_{1-4}$alkyl)aminosulphonyl, N—($C_{1-4}$alkyl)$_2$aminosulphonyl, N'—($C_{1-4}$alkyl)ureido or N'—($C_{1-4}$alkyl)$_2$ureido;

$R^8$ is $C_{1-6}$alkyl optionally substituted by one or more $R^{10}$, $C_{3-6}$cycloalkyl optionally substituted by one or more $R^{10}$, phenyl optionally substituted by one or more $R^{10}$, naphthyl optionally substituted by one or more $R^{10}$ or a heterocyclic group optionally substituted on a ring carbon by one or more $R^{10}$ and if said heterocyclic group contains an —NH— moiety that nitrogen may be optionally substituted by a group selected from D;

$R^9$ is phenyl optionally substituted by one or more $R^{10}$, naphthyl optionally substituted by one or more $R^{10}$ or a heterocyclic group optionally substituted on a ring carbon by one or more $R^{10}$ and if said heterocyclic group contains an —NH— moiety that nitrogen may be optionally substituted by a group selected from D;

$R^{10}$ is $C_{1-6}$alkyl-M— optionally substituted by $R^{16}$, halo, hydroxy, cyano, formyl, amino, nitro, carboxy, carbamoyl, thiol, sulphamoyl, phenyl optionally substituted by $R^{16}$, a heterocyclic group optionally substituted on a ring carbon by $R^{16}$ wherein if said heterocyclic group contains an —NH— moiety that nitrogen may be optionally substituted by a group selected from D;

Q is $C_{1-6}$alkyl-M— optionally substituted with one or more $R^{11}$, $C_{2-6}$alkenyl-M— optionally substituted by one or more $R^{11}$, $C_{2-6}$alkynyl-M— optionally substituted by one or more $R^{11}$, $R^{13}$—M—, hydroxy, halo, cyano, thiol, sulphamoyl, nitro, carboxy, amino, carbamoyl, formyl or ureido;

T is —O—, —C(O)—, —NH—, —N(N—$C_{1-6}$alkyl)-, —C(O)NH—, —NHC(O)—, —C(O)N(N—$C_{1-6}$alkyl)-, —N(N—$C_{1-6}$alkyl)C(O)—, —SO$_2$—, —C(S)—, —C(S)NH—, —NHC(S)—, —C(S)N(N—$C_{1-6}$alkyl)- or —N(N—$C_{1-6}$alkyl)C(S)—;

M is —O—, —N($R^{14}$)—, —C(O)—, —N($R^{14}$)C(O)—, —C(O)N($R^{14}$)—, —S(O)$_n$— wherein n is 0–2, —OC(O)—, —C(O)O—, —N($R^{14}$)C(O)O—, —OC(O)N($R^{14}$)—, —C(S)N($R^{14}$)—, —N($R^{14}$)C(S)—, —SO$_2$N($R^{14}$)—, —N($R^{14}$)SO$_2$—, —N($R^{14}$)C(O)N($R^{14}$)—, —N($R^{14}$)C(S)N($R^{14}$)—, —SO$_2$NHC(O)—, —SO$_2$N($R^{14}$)C(O)—, —C(O)NHSO$_2$—, —C(O)N($R^{14}$)SO$_2$— or M is a direct bond;

D is $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N—($C_{1-6}$alkyl)$_2$carbamoyl, benzoyl, (heterocyclic group)carbonyl, phenylsulphonyl, (heterocyclic group)sulphonyl, phenyl or a carbon linked heterocyclic group, and wherein any $C_{1-6}$alkyl group may be optionally substituted by one or more $R^{11}$, and wherein any phenyl or heterocyclic group may be optionally substituted on a ring carbon by one or more groups selected from $R^{10}$ and if a heterocyclic group contains an —NH— moiety that nitrogen may be optionally substituted by a group selected from E;

E is $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N—($C_{1-6}$alkyl)$_2$carbamoyl, $C_{1-6}$alkoxy$C_{1-6}$alkanoyl, phenyl$C_{1-6}$alkyl, benzoyl, phenyl$C_{1-6}$alkanoyl, phenyl$C_{1-6}$alkoxycarbonyl or phenylsulphonyl.

$R^{11}$ is hydroxy, nitro, cyano, thiol, halo, ureido, amino, N—($C_{1-6}$alkyl)amino, N—($C_{1-6}$alkyl)$_2$amino, carboxy, $C_{1-6}$alkoxy, carbamoyl, N—($C_{1-6}$alkyl)carbamoyl, N—($C_{1-6}$alkyl)$_2$carbamoyl, formyl, sulphamoyl, N—$C_{1-6}$alkylaminosulphonyl, N—($C_{1-6}$alkyl)$_2$aminosulphonyl, $C_{1-6}$alkylsulphonylamino, $C_{1-6}$alkanoylamino, $C_{1-6}$alkylsulphanyl, $C_{1-6}$alkylsulphinyl, $C_{1-6}$alkylsulphonyl, phenyl optionally substituted by one or more $R^{10}$, naphthyl optionally substituted by one or more $R^{10}$, or a heterocyclic group optionally substituted on a ring carbon by one or more $R^{10}$ and if said heterocyclic group contains an —NH— moiety that nitrogen may be optionally substituted by a group selected from D;

$R^{13}$ is phenyl optionally substituted by one or more $R^{10}$, $C_{3-6}$cycloalkyl optionally substituted by one or more $R^{10}$, naphthyl optionally substituted by one or more $R^{10}$, or a heterocyclic group optionally substituted on a ring carbon by one or more $R^{10}$ and if said heterocyclic group contains an —NH— moiety that nitrogen may be optionally substituted by a group selected from D;

$R^{14}$ is hydrogen or $C_{1-6}$alkyl optionally substituted by one or more $R^{15}$ with the proviso that $R^{15}$ is not a substituent on the carbon attached to the nitrogen atom of M;

$R^{15}$ is halo, hydroxy, amino, cyano, nitro, trifluoromethyl, trifluoromethoxy, $C_{1-6}$alkyl, $C_{2-6}$alkenyl, $C_{2-6}$alkynyl, N—($C_{1-6}$alkyl)amino, N—($C_{1-6}$alkyl)$_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoyl, N—($C_{1-6}$alkyl)aminosulphonyl, N—($C_{1-6}$alkyl)$_2$ aminosulphonyl, carboxy, carbamoyl, N—($C_{1-6}$alkyl)carbamoyl, N—($C_{1-6}$alkyl)$_2$carbamoyl, $C_{1-6}$alkoxycarbonyl, $C_{1-6}$alkanoyl or formyl;

$R^{16}$ is hydroxy, halo, cyano, $C_{1-6}$alkoxy, formyl, $C_{1-6}$alkanoyl, $C_{1-6}$alkanoyloxy, amino, N—($C_{1-6}$alkyl)amino, N—($C_{1-6}$alkyl)$_2$amino, $C_{1-6}$alkanoylamino, $C_{1-6}$alkanoyl(N—$C_{1-6}$alkyl)amino, carboxy, carbamoyl, $C_{1-6}$alkoxycarbonyl, $C_{1-6}$alkylsulphanyl, $C_{1-6}$alkylsulphinyl, $C_{1-6}$alkylsulphonyl, sulphamoyl, N—($C_{1-6}$alkyl)aminosulphonyl or N—($C_{1-6}$alkyl)$_2$aminosulphonyl;

and wherein if one of $R^5$, $R^6$ and $R^7$ is hydrogen the others cannot be hydrogen;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "halo$C_{1-6}$alkyl" includes halo$C_{1-4}$alkyl, trifluoromethyl, 1-chloroethyl and 2-fluoroethyl. The term "halo" refers to fluoro, chloro, bromo and iodo. Where a phrase such as "any $C_{1-6}$alkyl group may be optionally substituted by one or more groups" for the avoidance of doubt, it is to be understood that this refers to all groups that contain a $C_{1-6}$alkyl group, for example this phrase would also relate to a $C_{1-6}$alkanoyl group if that was listed in the paragraph.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —CH$_2$— group can optionally be replaced by a —C(O)—, and a ring nitrogen and/or a ring sulphur atom may be optionally oxidised to form an N- and/or an S-oxide. Suitable values for a "heterocyclic group" include azetidinyl, morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, tetrahydropyranyl, imidazolyl, pyrimidyl, pyrazinyl, pyridazinyl, isoxazolyl, 4-pyridone, 1-isoquinolone, 2-pyrrolidone and 4-thiazolidone.

A "carbon-linked 5-or 6-membered heteroaryl ring containing 1–3 heteroatoms" is a fully unsaturated monocyclic ring containing 5 or 6 atoms of which 1–3 are chosen from nitrogen, sulphur or oxygen. Suitable values for "a carbon-linked 5-or 6-membered heteroaryl ring containing 1–3 heteroatoms" include pyridyl, pyrimidyl, pyrazinyl, pyridadzinyl, pyrrolyl, furyl, thienyl, pyrazolyl, imidazolyl and triazolyl.

A "a carbon-linked 6-membered heteroaryl ring containing 1–2 nitrogen atoms" is a fully unsaturated monocyclic ring containing 6 atoms of which 1–2 are nitrogen. Suitable values for "a carbon-linked 6-membered heteroaryl ring containing 1–2 nitrogen atoms" include pyridyl, pyrimidyl, pyrazinyl and pyridadzinyl.

"Het" is a saturated, partially saturated or fully unsaturated, mono or bicyclic ring containing 4–12 atoms, one atom of which is the nitrogen atom to which $R^1$ and $R^2$ are attached to, and the other atoms are either all carbon atoms or they are carbon atoms and 1–3 heteroatoms chosen from nitrogen, sulphur or oxygen, wherein a —CH$_2$— group can optionally be replaced by a —C(O)—, and a ring nitrogen and/or a ring sulphur atom may be optionally oxidised to form an N- and/or an S-oxide. It will be appreciated that where $R^1$ and $R^2$ together with the nitrogen atom to which they are attached form a group Het this nitrogen atom is not quaternised, i.e. a neutral compound is formed. Suitable values for "a group Het" include azetidinyl, morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl and triazolyl. Preferably "a group Het" is morpholino, piperidyl, piperazinyl, pyrrolidinyl, thiomorpholino, pyrrolinyl or homopiperazinyl.

"Saturated Het" is a saturated mono or bicyclic ring containing 5–7 atoms, one atom of which is the nitrogen atom to which $R^1$ and $R^2$ are attached to, and the other atoms are either all carbon atoms or they are carbon atoms and 1 nitrogen atom, wherein a —CH$_2$— group can optionally be replaced by a —C(O)—. It will be appreciated that where $R^1$ and $R^2$ together with the nitrogen atom to which they are attached form a group "saturated Het" this nitrogen atom is not quaternised, i.e. a neutral compound is formed. Suitable values for "saturated Het" include morpholino, piperidyl, piperazinyl, pyrrolidinyl, thiomorpholino, homopiperazinyl, imidazolidinyl and pyrazolidinyl. Preferably "saturated Het" is morpholino, piperidyl or piperazinyl.

Examples of "$C_{1-6}$alkanoyloxy" are $C_{1-4}$alkanoyloxy and acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, methoxy, ethoxy and propoxy. Examples of "$C_{1-6}$alkanoylamino" include $C_{1-4}$alkanoylamino, acetamido and propionylamino. Examples of "$C_{1-6}$ alkylsulphanyl" include $C_{1-4}$alkylsulphanyl, methylthio and ethylthio. Examples of "$C_{1-6}$alkylsulphinyl" include $C_{1-4}$alkylsulphinyl, methylsulphinyl and ethylsulphinyl. Examples of "$C_{1-6}$ alkylsulphonyl" include $C_{1-4}$alkylsulphonyl, mesyl and ethylsulphonyl. Examples of "$C_{1-6}$alkanoyl" include $C_{1-4}$alkanoyl, propionyl and acetyl. Examples of "N—($C_{1-6}$alkyl)amino" include N—($C_{1-4}$alkyl)amino, methylamino and ethylamino. Examples of "N—($C_{1-6}$alkyl)$_2$amino" include N—($C_{1-4}$alkyl)$_2$amino, di-N-methylamino, di-(N-ethyl)amino and N-ethyl-N-methylamino. Examples of "$C_{2-6}$ alkenyloxy" are $C_{2-4}$alkenyloxy, vinyloxy and allyloxy. Examples of "$C_{3-6}$ cycloalkyl" are cyclopropyl and cyclohexyl. Examples of "$C_{2-6}$alkenyl" are $C_{2-4}$alkenyl, vinyl, allyl and 1-propenyl. Examples of "$C_{2-6}$alkynyl" are $C_{2-4}$alkynyl, ethynyl, 1-propynyl and 2-propynyl. Examples of "halo$C_{1-6}$alkoxy" are halo$C_{1-4}$alkoxy, trifluoromethoxy, 2-fluoroethoxy and 1-bromopropoxy. Examples of "$C_{1-6}$alkanoyl(N—$C_{1-6}$alkyl)amino" are $C_{1-4}$alkanoyl(N—$C_{1-4}$ alkyl)amino and (N-propyl)acetamido. Examples of "$C_{1-6}$ alkylsulphonylamino" are methylsulphonylamino and ethylsulphonylamino. Examples of "$C_{1-6}$alkylsulphonyl(N—$C_{1-6}$alkyl)amino" are $C_{1-4}$alkylsulphonyl(N—$C_{1-4}$alkyl)amino, methylsulphonyl-(N-ethyl)-amino and ethylsulphonyl-(N-butyl)-amino. Examples of "N—($C_{1-6}$ alkyl)aminosulphonyl" are N—($C_{1-4}$alkyl)aminosulphonyl, N-(methyl)aminosulphonyl and N-(ethyl)aminosulphonyl. Examples of "N—($C_{1-6}$alkyl)$_2$aminosulphonyl" are N—($C_{1-4}$ alkyl)$_2$aminosulphonyl, N-(dimethyl)aminosulphonyl and N-(methyl)-N-(ethyl)aminosulphonyl. Examples of "N—($C_{1-6}$alkyl)carbamoyl" are N—($C_{1-4}$alkyl)carbamoyl, methylaminocarbonyl and ethylaminocarbonyl. Examples of "N—(C$_{1-6}$alkyl)$_2$carbamoyl" are N—(C$_{1-4}$alkyl)$_2$carbamoyl, dimethylaminocarbonyl and methylethylaminocarbonyl. Examples of "N'—(C$_{1-4}$alkyl) ureido" are N'-methylureido and N'-ethylureido. Examples of "N'—(C$_{1-4}$alkyl)$_2$ureido" are N',N'-dimethylureido and N'-methyl-N'-ethylureido. Examples of "C$_{1-6}$ alkanoylaminosulphonyl" are C$_{1-4}$alkanoylaminosulphonyl, acetylaminosulphonyl and propionylaminosulphonyl. Examples of "C$_{1-6}$alkanoyl(N—C$_{1-6}$alkyl)aminosulphonyl" are C$_{1-4}$alkanoyl(N—C$_{1-4}$alkyl)aminosulphonyl, acetyl(N-methyl)aminosulphonyl and propionyl(N-ethyl) aminosulphonyl. Examples of "C$_{1-6}$ alkylsulphonylaminocarbonyl" are C$_{1-4}$alkylsulphonylaminocarbonyl, mesylaminocarbonyl and ethanesulphonylaminocarbonyl. Examples of "C$_{1-6}$alkylsulphonyl(N—C$_{1-6}$alkyl) aminocarbonyl" are C$_{1-4}$alkylsulphonyl(N—C$_{1-4}$alkyl) aminocarbonyl, N-(methyl)mesylaminocarbonyl and N-(methyl)ethanesulphonylaminocarbonyl. Examples of "(heterocyclic group)carbonyl" are pyridylcarbonyl and pyrimidylcarbonyl. Examples of "(heterocyclic group) sulphanyl" are pyridylsulphanyl and pyrimidylsulphanyl. Examples of "(heterocyclic group)sulphinyl" are pyridylsulphinyl and pyrimidylsulphinyl. Examples of "(heterocyclic group)sulphonyl" are pyridylsulphonyl and pyrimidylsulphonyl. Examples of "N-(heterocyclic group)amino" are N-pyridylamino and N-pyrimidylamino. Examples of "N-(heterocyclic group)carbonylamino" are N-pyridylcarbonylamino and N-pyrimidylcarbonylamino. Examples of "(heterocyclic group)sulphonylamino" are pyridylsulphonylamino and pyrimidylsulphonylamino. Examples of "N-(heterocyclic group)aminosulphonyl" are N-pyridylaminosulphonyl and N-pyrimidylaminosulphonyl. Examples of "N-(heterocyclic group)-N—(C$_{1-4}$alkyl) aminosulphonyl" are N-pyridyl-N-methylaminosulphonyl and pyrimidyl-N-ethylaminosulphonyl. Examples of "N-(heterocyclic group)carbamoyl" are N-pyridylcarbamoyl and N-pyrimidylcarbamoyl. Examples of "N-(heterocyclic group)-N—(C$_{1-4}$alkyl)carbamoyl" are N-pyridyl-N-methylcarbamoyl and N-pyrimidyl-N-ethylcarbamoyl. Examples of "N-phenyl-N—(C$_{1-4}$alkyl)aminosulphonyl" are N-phenyl-N-methylaminosulphonyl and N-phenyl-N-ethylaminosulphonyl. Examples of "phenylC$_{1-4}$alkanoylamino" include phenylacetamido and phenylpropionylamino. Examples of "N-phenyl-N—(C$_{1-4}$alkyl) carbamoyl" are N-phenyl-N-methylcarbamoyl and N-phenyl-N-ethylcarbamoyl.

Preferred values of R$^1$, R$^2$, R$^3$, R$^4$, R$^5$, R$^6$ and R$^7$ are as follows. Such values may be used where appropriate with any of the definitions, claims or embodiments defined hereinbefore or hereinafter.

Preferably R$^1$ and R$^2$ are each selected independently from hydrogen, phenyl optionally substituted by one or more Q, C$_{1-6}$alkyl optionally substituted by one or more Q, R$^8$T— and a heterocyclic group optionally substituted on a ring carbon by one or more Q and wherein if said heterocyclic group contains an —NH— moiety that nitrogen may be optionally substituted by a group selected from D, or R$^1$ and R$^2$ together with the nitrogen atom to which they are attached form a group Het which is optionally substituted on a ring carbon by one or more Q and wherein if group Het contains an —NH— moiety that nitrogen may be optionally substituted by a group selected from D.

More preferably R$^1$ and R$^2$ are each selected independently from hydrogen, phenyl optionally substituted by one or more Q, C$_{1-4}$alkyl optionally substituted by one or more Q, R$^8$T— and a carbon-linked 5-or 6-membered heteroaryl ring containing 1–3 heteroatoms optionally substituted by one or more Q, or R$^1$ and R$^2$ together with the nitrogen atom to which they are attached form a saturated Het which is optionally substituted on a ring carbon by one or more Q and wherein if said saturated Het contains an —NH— moiety that nitrogen may be optionally substituted by a group selected from D.

More preferably R$^1$ and R$^2$ are each selected independently from hydrogen, phenyl optionally substituted by one or more Q, C$_{1-4}$alkyl optionally substituted by one or more Q, R$^8$T— and a carbon-linked 6-membered heteroaryl ring containing 1–2 nitrogen atoms optionally substituted by one or more Q, or R$^1$ and R$^2$ together with the nitrogen atom to which they are attached form a saturated Het which is optionally substituted on a ring carbon by one or more Q and wherein if said saturated Het contains an —NH— moiety that nitrogen may be optionally substituted by a group selected from D.

In another aspect of the invention, preferably R$^1$ and R$^2$ are each selected independently from hydrogen, phenyl optionally substituted by one or more Q, C$_{3-6}$cycloalkyl optionally substituted by one or more Q, C$_{1-6}$alkyl optionally substituted by one or more Q, R$^8$T— and a heterocyclic group optionally substituted on a ring carbon by one or more Q and wherein if said heterocyclic group contains an —NH— moiety that nitrogen may be optionally substituted by a group selected from D, or R$^1$ and R$^2$ together with the nitrogen atom to which they are attached form a group Het which is optionally substituted on a ring carbon by one or more Q and wherein if group Het contains an —NH— moiety that nitrogen may be optionally substituted by a group selected from D.

In another aspect of the invention, more preferably R$^1$ and R$^2$ are each selected independently from hydrogen, phenyl optionally substituted by one or more Q, C$_{3-6}$cycloalkyl optionally substituted by one or more Q, C$_{1-4}$alkyl optionally substituted by one or more Q, R$^8$T— and a carbon-linked 5-or 6-membered heteroaryl ring containing 1–3 heteroatoms optionally substituted by one or more Q, or R$^1$ and R$^2$ together with the nitrogen atom to which they are attached form a saturated Het which is optionally substituted on a ring carbon by one or more Q and wherein if said saturated Het contains an —NH— moiety that nitrogen may be optionally substituted by a group selected from D.

In another aspect of the invention, particularly R$^1$ and R$^2$ are each selected independently from hydrogen, phenyl optionally substituted by one or more Q, C$_{3-6}$cycloalkyl optionally substituted by one or more Q, C$_{1-4}$alkyl optionally substituted by one or more Q, R$^8$T— and a carbon-linked 6-membered heteroaryl ring containing 1–2 nitrogen atoms optionally substituted by one or more Q, or R$^1$ and R$^2$ together with the nitrogen atom to which they are attached form a saturated Het which is optionally substituted on a ring carbon by one or more Q and wherein if said saturated Het contains an —NH— moiety that nitrogen may be optionally substituted by a group selected from D.

In a further aspect of the invention, preferably R$^1$ and R$^2$ are each selected independently from hydrogen, phenyl optionally substituted by one or more Q, C$_{3-6}$cycloalkyl optionally substituted by one or more Q, C$_{1-6}$alkyl optionally substituted by one or more Q and a heterocyclic group optionally substituted on a ring carbon by one or more Q, or $R^1$ and $R^2$ together with the nitrogen atom to which they are attached form a group Het which is optionally substituted on a ring carbon by one or more Q.

In a further aspect of the invention, more preferably $R^1$ and $R^2$ are each selected independently from hydrogen, phenyl optionally substituted by one or more Q, $C_{3-6}$cycloalkyl optionally substituted by one or more Q, $C_{1-4}$alkyl optionally substituted by one or more Q and a carbon-linked 5-or 6-membered heteroaryl ring containing 1–3 heteroatoms optionally substituted on a ring carbon by one or more Q, or $R^1$ and $R^2$ together with the nitrogen atom to which they are attached form a saturated Het which is optionally substituted on a ring carbon by one or more Q.

In a further aspect of the invention, particularly $R^1$ and $R^2$ are each selected independently from hydrogen, phenyl optionally substituted by one or more Q, $C_{3-6}$cycloalkyl optionally substituted by one or more Q, $C_{1-4}$alkyl optionally substituted by one or more Q and a carbon-linked 6-membered heteroaryl ring containing 1–2 nitrogen atoms optionally substituted on a ring carbon by one or more Q, or $R^1$ and $R^2$ together with the nitrogen atom to which they are attached form a saturated Het which is optionally substituted on a ring carbon by one or more Q.

Preferably $R^8$ is $C_{1-6}$alkyl and phenyl optionally substituted by one or more $R^{10}$.

More preferably $R^8$ is $C_{1-4}$alkyl and phenyl optionally substituted by one $R^{10}$.

Particularly $R^8$ is methyl and 4-methoxyphenyl.

Preferably Q is $C_{1-6}$alkyl-M— optionally substituted with one or more $R^{11}$, $R^{13}$—M—, hydroxy, halo, sulphamoyl, amino, carbamoyl or ureido.

More preferably Q is $C_{1-4}$alkyl-M— optionally substituted with one or more $R^{11}$, $R^{13}$—M—, hydroxy, halo, sulphamoyl, amino, carbamoyl or ureido.

Particularly Q is Me—M— optionally substituted with one or more $R^{11}$, $R^{13}$—M—, hydroxy, halo, sulphamoyl, amino, carbamoyl or ureido.

More particularly Q is hydroxy or methyl.

Particularly preferred Q is hydroxy.

In another aspect of the invention, preferably Q is hydroxy, acetamido, acetyl, dimethylamino, methoxy or methyl.

Preferably T is —C(O)—.

Preferably M is —O—, —N($R^{14}$)—, —N($R^{14}$)C(O)—, —C(O)N($R^{14}$)—, —S(O)$_n$—, wherein n is 1–2, —OC(O)— or —SO$_2$N($R^{14}$)— or M is a direct bond.

In one aspect of the invention, preferably M is —O—, —N($R^{14}$)—, —N($R^{14}$)C(O)—, —C(O)N($R^{14}$)—, —S(O)$_n$— wherein n is 1–2, —OC(O)— or —SO$_2$N($R^{14}$)—.

In another aspect of the invention, preferably M is a direct bond.

Preferably D is $C_{1-6}$alkanoyl, $C_{1-6}$alkylsulphonyl, N—($C_{1-6}$alkyl)$_2$carbamoyl, phenyl or a carbon linked heterocyclic group.

More preferably D is $C_{1-4}$alkanoyl, $C_{1-4}$alkylsulphonyl, N—($C_{1-4}$alkyl)$_2$carbamoyl, phenyl or a carbon linked heterocyclic group.

Particularly D is acetyl, mesyl, N,N-dimethylcarbamoyl, phenyl, pyridyl or pyrimidyl.

More particularly D is acetyl.

Preferably $R^{13}$ is phenyl or a heterocyclic group.

Preferably $R^{14}$ is hydrogen or $C_{1-4}$alkyl optionally substituted by one or more $R^{15}$ with the proviso that $R^{15}$ is not a substituent on the carbon attached to the nitrogen atom of M.

Preferably $R^{15}$ is hydroxy.

Therefore preferably $R^1$ and $R^2$ are each selected independently from hydrogen, phenyl {optionally substituted by one or more methoxy, fluoro, carbamoyl, acetylamino, sulphamoyl, methylsulphinyl, mesyl, methoxycarbonyl, methyl, amino, methylamino, ureido, hydroxy, chloro, acetyl, N-methylcarbamoyl and mesylamino}, $C_{1-6}$alkyl {optionally substituted by one or more hydroxy, methoxy, N,N-dimethylamino, acetylamino and N,N-dimethylcarbamoyl}, $C_{1-6}$alkanoyl, and a heterocyclic group {optionally substituted on a ring carbon by one or more hydroxy, methoxy, N,N-dimethylamino and methyl}, or $R^1$ and $R^2$ together with the nitrogen atom to which they are attached form a group Het which is optionally substituted on a ring carbon by one or more hydroxy and wherein if group Het contains an —NH— moiety that nitrogen may be optionally substituted by a group selected from acetyl, mesyl, phenyl, a carbon linked heterocyclic group and N,N-dimethylcarbamoyl.

Therefore more preferably $R^1$ and $R^2$ are each selected independently from hydrogen, $C_{1-6}$alkyl {optionally substituted by one or more hydroxy}, phenyl {optionally substituted by methoxy} and pyridyl optionally substituted on a ring carbon by methyl, or $R^1$ and $R^2$ together with the nitrogen atom to which they are attached form a piperidinyl, pyrrolidinyl or azetidinyl ring which is optionally substituted on a ring carbon by one or more hydroxy.

Therefore in one aspect of the invention particularly $R^1$ and $R^2$ are each selected independently from hydrogen, 2-hydroxypropyl, 2-hydroxy-2-methylpropyl, 3-hydroxybutyl, or $R^1$ and $R^2$ together with the nitrogen atom to which they are attached form a 4-hydroxypiperidinyl, 3-hydroxypiperidinyl, 3-hydroxypyrolidinyl or 3-hydroxyazetidinyl ring.

Therefore in one aspect of the invention more particularly one of $R^1$ and R2 is hydrogen, and the other is selected from 2-hydroxypropyl, 2-hydroxy-2-methylpropyl, 3-hydroxybutyl, or $R^1$ and $R^2$ together with the nitrogen atom to which they are attached form a 4-hydroxypiperidinyl, 3-hydroxypiperidinyl, 3-hydroxypyrolidinyl or 3-hydroxyazetidinyl ring.

Therefore in another aspect of the invention particularly $R^1$ and $R^2$ are each selected independently from hydrogen, methyl, 2-hydroxypropyl, 4-methoxyphenyl, 5-methylpyridyl, or $R^1$ and $R^2$ together with the nitrogen atom to which they are attached form a 4-hydroxypiperidinyl ring.

In another aspect of the invention, more particularly $R^1$ and $R^2$ are each selected independently from hydrogen, phenyl, 4-methoxyphenyl, 4-acetylphenyl, 4-acetamidophenyl, 4-dimethylaminophenyl, methyl, ethyl, isopropyl, 4-hydroxycyclohexyl, 1-methyl-2-hydroxyethyl, 1,1-dimethyl-2-hydroxyethyl, 2-hydroxyethyl, 2-hydroxypropyl, 2,3-dihydroxypropyl, pyrid-3-yl and 5-methylpyrid-2-yl, or $R^1$ and $R^2$ together with the nitrogen atom to which they are attached form 3-hydroxypyrrolidin-1-yl, 3-hydroxypiperidin-1-yl, 4-hydroxypiperidin-1-yl or morpholino.

In a further aspect of the invention, more particularly $R^1$ and $R^2$ are each selected independently from hydrogen, phenyl, 4-methylphenyl, 2-methoxyphenyl, 4-methoxyphenyl, 4-acetylphenyl, 4-acetamidophenyl, 4-dimethylaminophenyl, 2,4-dimethoxyphenyl, 3,4-dimethoxyphenyl, methyl, ethyl, isopropyl, 4-hydroxycyclohexyl, 1-methyl-2-hydroxyethyl, 1,1-dimethyl-2-hydroxyethyl, 2-hydroxyethyl, 2-hydroxypropyl, 2,3-dihydroxypropyl, pyrid-3-yl and 5-methylpyrid-2-yl, 2-methoxypyrid-5-yl, or $R^1$ and $R^2$ together with the nitrogen atom to which they are attached form 3-hydroxypyrrolidin-1-yl, 3-hydroxypiperidin-1-yl, 4-hydroxypiperidin-1-yl or morpholino.

In a further aspect of the invention, more particularly $R^1$ and $R^2$ are each selected independently from hydrogen, methyl, 1-methyl-2-hydroxyethyl or 2-hydroxypropyl.

In a further aspect of the invention, particularly preferred $R^1$ and $R^2$ are each selected independently from hydrogen, methyl, (R,S)-1-methyl-2-hydroxyethyl, (S)-1-methyl-2-hydroxyethyl, (R)-1-methyl-2-hydroxyethyl, (R,S)-2-hydroxypropyl, (S)-2-hydroxypropyl or (R)-2-hydroxypropyl.

In a further aspect of the invention, more particularly preferred one of $R^1$ and $R^2$ is hydrogen and the other is selected from methyl, (R,S)-1-methyl-2-hydroxyethyl, (S)-1-methyl-2-hydroxyethyl, (R)-1-methyl-2-hydroxyethyl, (R,S)-2-hydroxypropyl, (S)-2-hydroxypropyl or (R)-2-hydroxypropyl.

Preferably the $R^1R^2NSO_2$— group is ortho to $R^7$.

In one aspect of the invention $R^3$ and $R^4$ are independently $C_k$alkyl optionally substituted by from 1 to 2k+1 atoms selected from fluoro and chloro wherein k is 1–3.

Preferably $R^3$ and $R^4$ are independently $C_k$alkyl optionally substituted by from 1 to 2k+1 atoms selected from fluoro and chloro, wherein k is 1–3, or $R^3$ and $R^4$, together with the carbon atom to which they are attached, form a cyclopropane ring optionally substituted by from 1 to 4 fluorine atoms.

More preferably $R^3$ and $R^4$ are independently $C_k$alkyl optionally substituted by from 1 to 2k+1 fluorine atoms, wherein k is 1–2, or $R^3$ and $R^4$, together with the carbon atom to which they are attached, form a cyclopropane ring optionally substituted by from 1 to 4 fluorine atoms.

Particularly $R^3$ and $R^4$ are independently methyl, fluoromethyl, difluoromethyl, trifluoromethyl, 2,2,2-trifluoroethyl and perfluoroethyl, or $R^3$ and $R^4$, together with the carbon atom to which they are attached, form a cyclopropane ring optionally substituted by from 1 to 4 fluorine atoms.

More particularly $R^3$ and $R^4$ are independently methyl, fluoromethyl, difluoromethyl and trifluoromethyl, or $R^3$ and $R^4$, together with the carbon atom to which they are attached, form a cyclopropane ring optionally substituted by from 1 to 4 fluorine atoms.

Preferred combinations of $R^3$ and $R^4$ are as follows.

Preferably $R^3$ and $R^4$ are both methyl or one of $R^3$ and $R^4$ is methyl and the other is trifluoromethyl.

More preferably one of $R^3$ and $R^4$ is methyl and the other is trifluoromethyl.

Preferably $R^5$ is selected from halo, haloC$_{1-4}$alkyl, haloC$_{1-4}$alkoxy, nitro, C$_{1-4}$alkyl, C$_{1-4}$alkoxy, C$_{2-4}$alkenyl, C$_{2-4}$alkynyl, hydroxy, hydrogen, amino, cyano, carboxy and sulphamoyl.

More preferably $R^5$ is selected from fluoro, chloro, bromo, nitro, methyl, ethyl, methoxy, ethoxy, ethenyl, ethynyl, hydroxy, hydrogen, amino, cyano, carboxy, sulphamoyl, trifluoromethyl and trifluoromethoxy.

Particularly $R^5$ is selected from fluoro, bromo, chloro, nitro, methyl, ethenyl and ethynyl.

More particularly $R^5$ is selected from fluoro, chloro, bromo and methyl.

Particularly preferred $R^5$ is selected from chloro and bromo.

More particularly preferred $R^5$ is selected from chloro.

In another aspect of the invention, preferably $R^5$ is selected from chloro or methoxy.

Preferably $R^6$ is Q.

In one aspect of the invention preferably $R^6$ is a heterocyclic group {optionally substituted on a ring carbon by one or more hydroxy, acetyl, halo, C$_{1-4}$alkylsulphonyl, C$_{1-4}$alkyl, N—(C$_{1-4}$alkyl)carbamoyl, N—(C$_{1-4}$alkyl)$_2$ carbamoyl and wherein if said heterocyclic group contains an —NH— moiety that nitrogen may be optionally substituted by a group selected from C$_{1-4}$alkyl, C$_{1-4}$alkylsulphonyl or C$_{1-4}$alkanoyl}, halo, hydroxy, trifluoromethyl, C$_{1-4}$alkyl, C$_{1-4}$alkoxy, C$_{1-4}$alkylsulphanyl, C$_{1-4}$alkylsulphinyl, C$_{1-4}$alkylsulphonyl, C$_{1-4}$alkylamino, N—(C$_{1-4}$alkyl)$_2$amino, C$_{1-4}$alkanoylamino, (C$_{1-4}$alkyl)sulphonylamino, N—(C$_{1-4}$alkyl)aminosulphonyl, N—(C$_{1-4}$alkyl)$_2$aminosulphonyl, N—(C$_{1-4}$alkyl)carbamoyl, N—(C$_{1-4}$alkyl)$_2$carbamoyl {wherein any C$_{1-4}$alkyl group may be optionally substituted by one or more hydroxy, methoxy, N,N-dimethylamino, amino, a heterocyclic group [wherein if said heterocyclic group contains an —NH— moiety that nitrogen may be optionally substituted by a group selected from methyl or acetyl], acetylamino and N,N-dimethylcarbamoyl}, (heterocyclic group)sulphanyl, (heterocyclic group)sulphinyl, (heterocyclic group)sulphonyl, N-(heterocyclic group)amino, (heterocyclic group)carbonylamino, (heterocyclic group)sulphonylamino, N-(heterocyclic group)aminosulphonyl, N-(heterocyclic group)N—(C$_{1-4}$alkyl)aminosulphonyl, N-(heterocyclic group)carbamoyl, N-(heterocyclic group)N—(C$_{1-4}$alkyl)carbamoyl {wherein any heterocyclic group may be optionally substituted on a ring carbon by one or more hydroxy, methoxy, N,N-dimethylamino, amino, a heterocyclic group [wherein if said heterocyclic group contains an —NH— moiety that nitrogen may be optionally substituted by a group selected from methyl, mesyl or acetyl], acetylamino, N,N-dimethylcarbamoyl, 2-hydroxyethylamino, acetyl, methylsulphinyl or methylsulphonyl and wherein if said heterocyclic group contains an —NH— moiety that nitrogen may be optionally substituted by a group selected from methyl, mesyl or acetyl}, phenylsulphanyl, phenylsulphinyl, phenylsulphonyl, N-phenylamino, phenylC$_{1-4}$alkanoylamino, phenylsulphonylamino, N-phenylaminosulphonyl, N-phenyl-N—(C$_{1-4}$alkyl)aminosulphonyl, N-phenylcarbamoyl, N-phenyl-N—(C$_{1-4}$alkyl)carbamoyl {wherein any phenyl group may be optionally substituted by one or more hydroxy, methoxy, N,N-dimethylamino, amino, a heterocyclic group [wherein if said heterocyclic group contains an —NH— moiety that nitrogen may be optionally substituted by a group selected from methyl or acetyl], acetylamino, N,N-dimethylcarbamoyl, 2-hydroxyethylamino, acetyl, methylsulphinyl or methylsulphonyl}.

In one aspect of the invention more preferably $R^6$ is pyrrolidine, piperidine, piperazine (optionally substituted on —NH— by a group selected from methyl, mesyl and acetyl) or pyridine {which pyrrolidine, piperidine, piperazine or pyridine may be optionally substituted on a ring carbon by one or more hydroxy, acetyl, mesyl, ethylsulphonyl, methyl, ethyl, methoxy, ethoxy, N-methylcarbamoyl, N-ethylcarbamoyl, N,N-dimethylcarbamoyl, N,N-diethylcarbamoyl, N-methyl-N-ethylcarbamoyl}, fluoro, chloro, bromo, hydroxy, trifluoromethyl, methyl, ethyl, methylthlio, ethylthio, methylsulphinyl, ethylsulphinyl, mesyl, ethylsulphonyl, methylamino, ethylamino, N,N-dimethylamino, N,N-diethylamino, N-methyl-N-ethylamino, acetylamino, propionylamino, mesylamino, ethylsulphonylamino, methylaminosulphonyl, ethylaminosulphonyl, N,N-dimethylaminosulphonyl, N,N-diethylaminosulphonyl, N-methyl-N-ethylaminosulphonyl, N-methylcarbamoyl, N-ethylcarbamoyl, N,N-dimethylcarbamoyl, N,N-diethylcarbamoyl, N-methyl-N-ethylcarbamoyl, {wherein any methyl or ethyl may be optionally substituted by one or more hydroxy, methoxy, N,N-dimethylamino, amino, piperazine, N-methylpiperazine, N-acetylpiperazine, morpholine, acetylamino and N,N-dimethylcarbamoyl}, pyridylsulphinyl, pyridylsulphonyl, N-pyridylamino, pyridylcarbonylamino, pyridylsulphonylamino, N-pyridylaminosulphonyl, N-pyridylcarbamoyl {wherein any pyridyl group may be optionally substituted on a ring carbon by one or more hydroxy, methoxy, N,N-dimethylamino, amino, piperazine, N-methylpiperazine, N-acetylpiperazine, morpholine, acetylamino, N,N-dimethylcarbamoyl, 2-hydroxyethylamino, acetyl, methylsulphinyl or methylsulphonyl}, phenylsulphinyl, phenylsulphonyl, N-phenylamino, benzoylamino, phenylsulphonylamino, N-phenylaminosulphonyl, N-phenylcarbamoyl {wherein any phenyl group may be optionally substituted by one or more hydroxy, methoxy, N,N-dimethylamino, amino, piperazine, N-methylpiperazine, N-acetylpiperazine, morpholine, acetylamino, N,N-dimethylcarbamoyl, 2-hydroxyethylamino, acetyl, methylsulphinyl or methylsulphonyl}.

In one aspect of the invention particularly $R^6$ is fluoro, chloro, acetamido and methylsulphanyl.

In another aspect of the invention preferably $R^6$ is hydrogen, halo, hydroxy, carbamoyl, $(C_{1-4}alkyl)_2$amino, $C_{1-4}$alkanoylamino, $(C_{1-4}alkyl)$sulphonylamino, N—($C_{1-4}$alkyl)aminosulphonyl, N—($C_{1-4}alkyl)_2$aminosulphonyl, N—($C_{1-4}$alkyl)carbamoyl, N—($C_{1-4}alkyl)_2$carbamoyl, $C_{1-4}$alkyloxy, $C_{1-6}$alkyl, $C_{1-4}$alkylamino, $C_{1-4}$alkylsulphinyl, $C_{1-4}$alkylsulphonyl {wherein any $C_{1-4}$alkyl may be optionally substituted by one or more halo, hydroxy, amino, carbamoyl, N,N-dimethylcarbamoyl, methylsulphinyl, methylsulphonyl, N-methylpiperazinyl or N-acetylpiperazinyl}, morpholino, piperazinyl {optionally substituted on —NH— with methyl, 2-hydroxyethyl or acetyl}, (heterocyclic group)sulphinyl, (heterocyclic group)sulphonyl {wherein any heterocyclic group is optionally substituted by one or more halo, hydroxy, 2-hydroxyethylamino, amino, carbamoyl, N,N-dimethylcarbamoyl, methylsulphinyl, methylsulphonyl, N-methylpiperazinyl or N-acetylpiperazinyl}, phenylsulphinyl, phenylsulphonyl {wherein any phenyl is optionally substituted by one or more halo, hydroxy, 2-hydroxyethylamino, amino, carbamoyl, N,N-dimethylcarbamoyl, methylsulphinyl, methylsulphonyl, N-methylpiperazinyl or N-acetylpiperazinyl }.

In another aspect of the invention more preferably $R^6$ is hydrogen, halo, hydroxy, carbamoyl, N,N-dimethylamino, N,N-diethylamino, N-methyl-N-ethylamino, acetylamino, propionylamino, mesylamino, ethylsulphonylamino, methylaminosulphonyl, ethylaminosulphonyl, N,N-dimethylaminosulphonyl, N,N-diethylaminosulphonyl, N-methyl-N-ethylaminosulphonyl, N-methylcarbamoyl, N-ethylcarbamoyl, N,N-dimethylcarbamoyl, N,N-diethylcarbamoyl, N-methyl-N-ethylcarbamoyl, methyl, ethyl, methoxy, ethoxy, methylamino, etlylamino, methylsulphinyl, ethylsulphinyl, mesyl, ethylsulphonyl {wherein any methyl or ethyl may be optionally substituted by one or more halo, hydroxy, amino, carbamoyl, N,N-dimethylcarbamoyl, methylsulphinyl, methylsuphonyl, N-methylpiperazinyl or N-acetylpiperazinyl}, morpholino, piperazinyl {optionally substituted on —NH— with optionally substituted on —NH— with methyl, 2-hydroxyethyl or acetyl}, (heterocyclic group)sulphinyl, (heterocyclic group) sulphonyl {wherein any heterocyclic group is optionally substituted by one or more halo, hydroxy, 2-hydroxyethylamino, amino, carbamoyl, N,N-dimethylcarbamoyl, methylsulphinyl, methylsulphonyl, N-methylpiperazinyl or N-acetylpiperazinyl}, phenylsulphinyl, phenylsulphonyl {wherein any phenyl is optionally substituted by one or more halo, hydroxy, 2-hydroxyethylamino, amino, carbamoyl, N,N-dimethylcarbamoyl, methylsulphinyl, methylsulphonyl, N-methylpiperazinyl or N-acetylpiperazinyl }.

In a further aspect of the invention, preferably $R^6$ is chloro.

In a further aspect of the invention, preferably $R^6$ is selected from hydrogen, chloro, iodo, methylsulphanyl or methyl.

In a further aspect of the invention, preferably $R^6$ is selected from chloro, iodo, methylsulphanyl or methyl.

In a further aspect of the invention, preferably $R^6$ is selected from chloro or methyl.

In one aspect of the invention, preferably $R^6$ is ortho to $R^5$.

In another aspect of the invention, preferably $R^6$ is ortho to $R^7$.

Preferably $R^7$ is hydrogen, $C_{1-4}$alkyl, halo and $C_{1-4}$alkoxy.

More preferably $R^7$ is hydrogen, methyl, fluoro, chloro and methoxy.

Particularly $R^7$ is hydrogen and fluoro.

More particularly $R^7$ is hydrogen.

In another aspect of the invention, preferably $R^7$ is hydrogen or methoxy.

Where —C(OH)($R^3$)($R^4$) represents a chiral center, the (R)-configuration is generally the preferred stereochemistry.

Therefore in a further aspect of the invention there is provided a compound of formula (I) (as depicted above) wherein:

$R^1$ and $R^2$ are each selected independently from hydrogen, phenyl optionally substituted by one or more Q, $C_{3-6}$cycloalkyl optionally substituted by one or more Q, $C_{1-6}$alkyl optionally substituted by one or more Q and a heterocyclic group optionally substituted on a ring carbon by one or more Q, or $R^1$ and $R^2$ together with the nitrogen atom to which they are attached form a group Het which is optionally substituted on a ring carbon by one or more Q;

Q is hydroxy, acetamido, acetyl, dimethylamino, methoxy or methyl;

$R^3$ and $R^4$ is methyl and the other is trifluoromethyl;

$R^5$ is selected from chloro or methoxy;

$R^6$ is selected from hydrogen, chloro, iodo, methylsulphanyl or methyl; and $R^7$ is hydrogen or methoxy;

or a pharmaceutically acceptable salt or an in vivo hydrolysable ester thereof.

Therefore in a further aspect of the invention there is provided a compound of formula (I'):

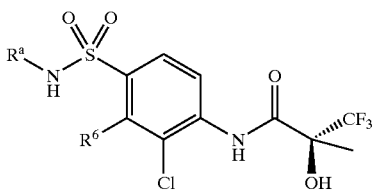

(I')

wherein:
R$^a$ is selected from methyl, (R,S)-1-methyl-2-hydroxyethyl, S)-1-methyl-2-hydroxyethyl, (R)-1-methyl-2-hydroxyethyl, (R,S)-2-hydroxypropyl, S)-2-hydroxypropyl or (R)-2-hydroxypropyl; and
R$^6$ is methyl or chloro;
or a pharmaceutically acceptable salt or an in vivo hydrolysable ester thereof.

A preferred compound of the invention is any one of the Examples or a pharmaceutically acceptable salt or an in vivo hydrolysable ester thereof.

More preferred compounds of the invention are any one of Examples 2, 8, 21, 26, 27, 40, 41 and 43 or a pharmaceutically acceptable salt or an in vivo hydrolysable ester thereof.

Preferred aspects of the invention are those which relate to the compound or a pharmaceutically acceptable salt thereof.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain one or more asymmetrically substituted carbon and/or sulphur atoms, and accordingly may exist in, and be isolated as enantiomerically pure, a mixture of diastereoisomers or as a racemate. Some compounds may exhibit polymorphism. It is to be understood that the present invention encompasses any racemic, optically-active, enantiomerically pure, mixture of diastereoisomers, polymorphic or stereoisomeric form, or mixtures thereof, which form possesses properties useful in the elevation of PDH activity, it being well known in the art how to prepare optically-active forms (for example, by resolution of the racemic form by recrystallization techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Another aspect of the present invention provides a process for preparing a compound of formula (I) or a pharmaceutically acceptable salt or an in vivo hydrolysable ester thereof, which process (in which variable groups are as defined for formula (I) unless otherwise stated) comprises of:

(a) deprotecting a protected compound of formula (II):

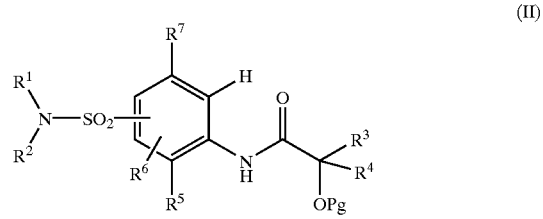

where Pg is an alcohol protecting group;
(b) coupling an aniline of formula (III):

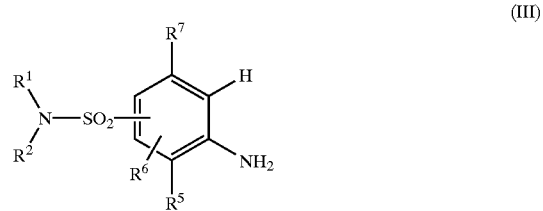

with an acid of formula (IV):

wherein G is a hydroxyl group;
(c) coupling an aniline of formula (III) with an activated acid derivative of formula (IV) wherein G is a hydroxyl group which may be protected as an ester, ether or silyl ether;
(d) reacting a compound of formula (V):

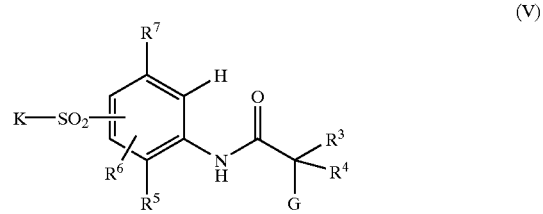

where K is a leaving atom or group and G is a hydroxyl group which may be protected as an ester; with an amine of formula (VI):

$$R^1R^2NH \qquad (VI);$$

and thereafter if necessary:
i) converting a compound of the formula (I) into another compound of the formula (I);
ii) removing any protecting groups; or
iii) forming a pharmaceutically acceptable salt or in vivo hydrolysable ester.

Suitable values for Pg are a benzyl group, a silyl group (for example a trialkylsilyl group or an alkyldiphenylsilyl group) or an acetyl protecting group.

K is a leaving atom or group, suitable values for K are for example a halogen atom such as fluoro or chloro.

Specific conditions of the above reactions are as follows:

Process a)

Suitable reagents for deprotecting an alcohol of formula (II) are for example:
1) when Pg is benzyl:
   (i) hydrogen in the presence of palladium/carbon catalyst, i.e. hydrogenolysis; or
   (ii) hydrogen bromide or hydrogen iodide;
2) when Pg is a silyl protecting group:
   (i) tetrabutylammonium fluoride; or
   (ii) aqueous hydrofluoric acid;
3) when Pg is acetyl:
   i) mild aqueous base for example lithium hydroxide; or
   ii) ammonia or an amine such as dimethylamine.

The reaction can be conducted in a suitable solvent such as ethanol, methanol, acetonitrile, or dimethyl sulphoxide and may conveniently be performed at a temperature in the range of −40 to 100° C.

Compounds of formula (II) may be prepared according to the following scheme:

E is a carboxy protecting group. Suitable values for E include $C_{1-6}$alkyl, such as methyl and ethyl.

Compounds of formula (IIa) are commercially available compounds, or they are known in the literature, or they are prepared by standard processes known in the art. The synthesis of compounds of formula (III) is described below.

Process b)

An aniline of formula (III) and an acid of formula (IV) may be coupled together in the presence of a suitable coupling reagent. Standard peptide coupling reagents known in the art can be employed as suitable coupling reagents, for example conditions such as those described above for the coupling of (IId) and (III), or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

A compound of formula (III) may be prepared according to Schemes 2) or 3):

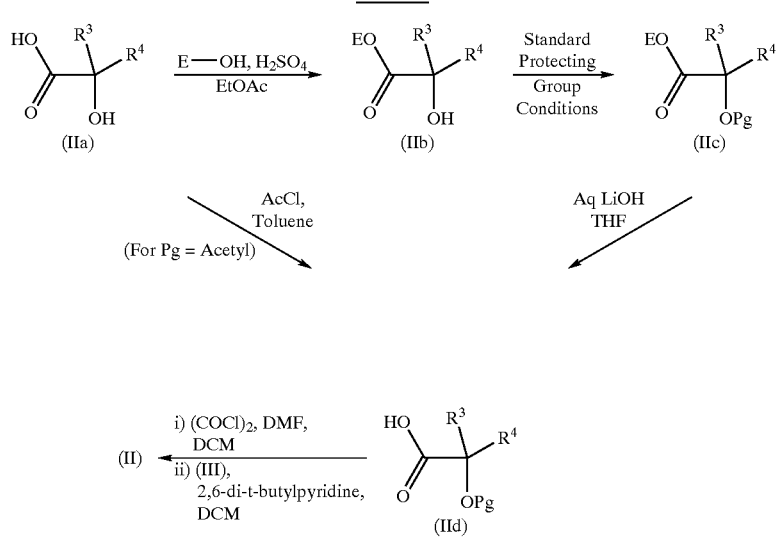

Scheme 3

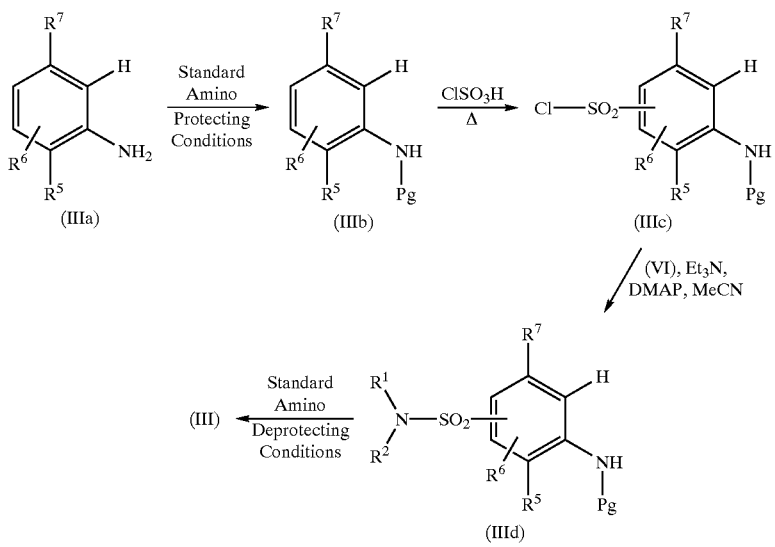

or:

Scheme 3

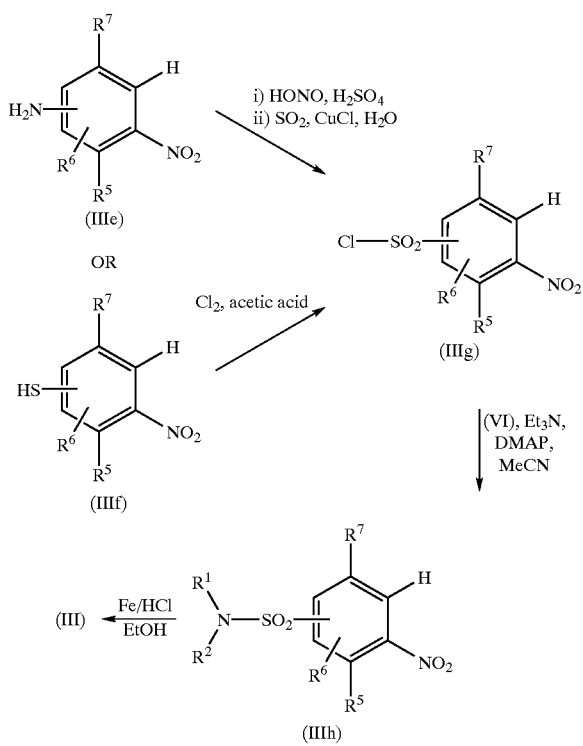

Compounds of formula (IIIa), (IIIe), (IIIf), (IV) and (VI) are commercially available compounds, or they are known in the literature, or they are prepared by standard processes known in the art.

If the resolved acid of formula (IV) is required it may be prepared by any of the known methods for preparation of optically-active forms (for example, by recrystallization of the chiral salt {for example WO 9738124}, by enzymatic resolution or by chromatographic separation using a chiral stationary phase). For example if an (R)-(+) resolved acid is required it may be prepared by the method of Scheme 2 in World Patent Application Publication No. WO 9738124 for preparation of the (S)-(−) acid, i.e. using the classical resolution method described in European Patent Application Publication No. EP 0524781, also for preparation of the (S)-(−) acid, except that (1S,2R)-norephedrine may be used in place of (S)-(−)-1-phenylethylamine. The chiral acid may also be prepared by using the enzymatic resolution method as described in Tetrahedron Asymmetry, 1999, 10, 679.

Process c)

An aniline of formula (III) may be coupled with an activated acid derivative of formula (IV) for example acid chlorides, acid anhydrides, or phenyl esters, wherein G is a hydroxyl group which may be suitably protected as a stable ester or ether (see above synthesis of formula (IId). This coupling may be achieved optionally in the presence of a base for example triethylamine, pyridine, or 2,6-di-alkylpyridines such as 2,6-lutidine or 2,6-di-tert-butylpyridine or 2,6-di-phenylpyridines. Suitable solvents include dimethylacetamide, dichloromethane, benzene, tetrahydrofuran, and dimethylformamide. The coupling reaction may conveniently be performed at a temperature in the range of −40 to 40° C.;

Process d)

A compound of formula (V) may be reacted with an amine of formula (VI) in the presence of a base, for example a tertiary amine such as triethylamine and in the presence of a catalyst for example dimethylaminopyridine. Suitable solvents for the reaction include acetonitrile and dimethylformamide. The reaction is conveniently performed at a temperature in the range of from 0 to 120° C.

A compound of formula (V) may be prepared according to the following scheme:

Scheme 4

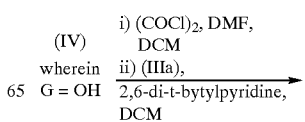

-continued

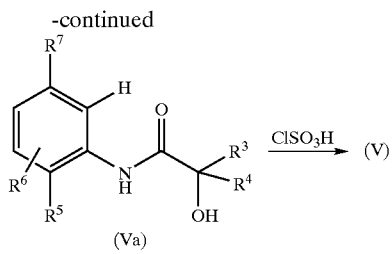

(Va)

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

For example, it will be appreciated that certain of the optional aromatic substituents in the compounds of the present invention may be introduced by standard aromatic substitution reactions or generated by conventional functional group modifications or interconversions either prior to or immediately following the processes mentioned above, and as such are included in the process aspect of the invention. Such reactions and modifications include, for example, introduction of a substituent by means of an aromatic substitution reaction, reduction of substituents alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by, for example, catalytic hydrogenation with a nickel catalyst or treatment with iron in the presence of hydrochloric acid with heating; oxidation of alkylthio to alkylsulphinyl or alkylsulphonyl using, for example, hydrogen peroxide in acetic acid with heating or 3-chloroperbenzoic acid. Particular examples of functional group interconversions are for example conversion of an aniline into a halophenyl by, for example, diazotisation in the presence of cuprous halides.

It is noted that many of the starting materials for synthetic methods as described above are commercially available and/or widely reported in the scientific literature, or could be made from commercially available compounds using adaptations of processes reported in the scientific literature.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as, for example hydrochloric sulphuric or phosphoric acid or trifluoroacetic acid and an arylmethoxycarbonyl group such as a benzyloxycarbonyl group may be removed, for example, by hydrogenation in the presence of a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation in the presence of a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, α-ketoglutarate, and α-glycerophosphate. Suitable inorganic salts may also be formed such as sulphate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g. sodium, potassium, or lithium) or alkaline earth metal (e.g. calcium) salt by treating a compound of formula (I) (and in some cases the ester) with one equivalent of an alkali metal or alkaline earth metal hydroxide or alkoxide (e.g. the ethoxide or methoxide) in aqueous medium followed by conventional purification techniques.

The compounds of the formula (I) may be administered in the form of a prodrug which is broken down in the human or animal body to give a compound of the formula (I). Examples of prodrugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable in vivo hydrolysable esters for a compound of the formula (I) containing a carboxy group include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-didxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable in vivo hydrolysable esters of a compound of the formula (I) containing a hydroxy group includes inorganic esters such as phosphate esters and α-acyloxyalkyl ethers. Examples of α-acyloxyalkyl ethers include acetoxymethoxy and 2,2-dimethylpropionyloxymethoxy. Other in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents for benzoyl include morpholino and piperazino linked from a ring nitrogen atom via a methylene group to the 3- or 4- position of the benzoyl ring.

In vivo cleavable prodrugs of compounds of formula (I) also include in vivo hydrolysable amides of compounds of the formula (I) containing a carboxy group, for example, a N—$C_{1-6}$alkyl or N—di—$C_{1-6}$alkyl amide such as N-methyl, N-ethyl, N-propyl, N-dimethyl, N-ethyl-N-methyl or N-diethyl amide.

The identification of compounds which elevate PDH activity is the subject of the present invention. These properties may be assessed, for example, using one or more of the procedures set out below:

(a) In vitro Elevation of PDH Activity

This assay determines the ability of a test compound to elevate PDH activity. cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in Escherichia coli (E. Coli), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into E. coli (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning —A Laboratory Manual, $2_{nd}$ edition, Cold Spring Harbour Laboratory Press. Other known PDH kinases for use in assays, may be cloned and expressed in a similar manner.

For expression of rPDHKII activity, E. coli strain M15pRep4 cells were transformed with the pQE32 vector containing rPDHKII cDNA. This vector incorporates a 6-His tag onto the protein at its N-terminus. E. coli were grown to an optical density of 0.6 (600 nM) and protein expression was induced by the addition of 10 µM isopropylthio-β-galactosidase. Cells were grown for 18 hours at 18° C. and harvested by centrifugation. The resuspended cell paste was lysed by homogenisation and insoluble material removed by centrifugation at 24000×g for 1 hour. The 6-His tagged protein was removed from the supernatant using a nickel chelating nitrilotriacetic acid resin (Ni-NTA: Quiagen Ltd.) matrix (Quiagen) which was washed with 20 mM tris(hydroxymethyl)aminomethane-hydrogen chloride, 20 mM imidazole, 0.5 M sodium chloride pH 8.0, prior to elution of bound protein using a buffer containing 20 mM tris(hydroxymethyl)aminomethane-hydrogen chloride, 200 mM imidazole, 0.15 M sodium chloride pH 8.0. Eluted fractions containing 6-His protein were pooled and stored in aliquots at −80° C. in 10% glycerol.

Each new batch of stock enzyme was titrated in the assay to determine a concentration giving approximately 90% inhibition of PDH in the conditions of the assay. For a typical batch, stock enzyme was diluted to 7.5 µg/ml.

For assay of the activity of novel compounds, compounds were diluted with 10% dimethyl sulphoxide (DMSO) and 10 µl transferred to individual wells of 96-well assay plates. Control wells contained 20 µl 10% DMSO instead of compound. 40 µl Buffer containing 50 mM potassium phosphate buffer pH 7.0, 10 mM ethylene glycol-bis(β-aminoethyl ether)-N,N-tetracetic acid (EGTA), 1 mM benzamidine, 1 mM phenylmethylsulphonyl fluoride (PMSF), 0.3 mM tosyl-L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 µM ATP, 2 mM magnesium chloride and 0.04 U/ml PDH (porcine heart PDH Sigma P7032) in a total volume of 50 µl and plates incubated at ambient temperature for a further 45 minutes. The residual activity of the PDH was then determined by the addition of substrates (2.5 mM coenzyme A, 2.5 mM thiamine pyrophosphate (cocarboxylase), 2.5 mM sodium pyruvate, 6 mM NAD in a total volume of 80 µl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In vitro Elevation of PDH Activity in Isolated Primary Cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 viable cells per well in Dulbecco's Modified Eagles Medium (DMEM, Gibco BRL) containing 10% foetal calf serum (FCS), 10% penicillin/ streptomycin (Gibco BRL) and 10% non-essential amino acids (NEAA, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexamethasone and 10 nM insulin.

The following day cells were washed with phosphate buffered saline (PBS) and medium replaced with 1 ml HEPES-buffered Krebs solution (25 mM HEPES, 0.15 M sodium chloride, 25 mM sodium hydrogen carbonate, 5 mM potassium chloride, 2 mM calcium chloride, 1 mM magnesium sulphate, 1 mM potassium dihydrogen phosphate) containing the compound to be tested at the required concentration in 0.1% DMSO. Control wells contained 0.1% DMS0 only and a maximum response was determined using a 10 $\mu$M treatment of a known active compound. After a preincubation period of 40 minutes at 37° C. in 5% $CO_2$, cells were pulsed with sodium pyruvate to a final concentration of 0.5 mM (containing 1-$^{14}$C sodium pyruvate (Amersham product CFA85) 0.18 Ci/mmole) for 12 minutes. The medium was then removed and transferred to a tube which was immediately sealed with a bung containing a suspended centre well. Absorbent within the centre well was saturated with 50% phenylethylamine, and $CO_2$ in the medium released by the addition of 0.2 $\mu$l 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In vivo Elevation of PDH Activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacpoole (1982) Biochem. Pharmacol.31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 $\mu$M phenylmethylsulphonyl chloride (PMSF) and 2 $\mu$g/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96):20 $\mu$l extract, 40 $\mu$l phosphatase (1:20 dilution), in a final volume of 125 $\mu$l containing 25 mM magnesium chloride, 1 mM calcium chloride. The activity of the untreated sample is compared with the activity of the dephosphorylated extract thus prepared. PDH activity is assayed by the method of Stansbie et al., (Biochem. J. (1976) 154, 225). 50 $\mu$l Extract is incubated with 0.75 mM NAD, 0.2 mM CoA, 1.5 mM thiamine pyrophosphate (TPP) and 1.5 mM sodium pyruvate in the presence of 20 $\mu$g/ml p-(p-amino-phenylazo) benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8. AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phiosphatase).

According to a further aspect of the invention there is provided a pharmaceutical composition which comprises a, compound of the formula (I) as defined hereinbefore or a pharmaceutically acceptable salt or an in vivo hydrolysable ester thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable salt or an in vivo hydrolysable ester thereof as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I) and pharmaceutically acceptable salts or in vivo hydrolysable esters thereof for use as a medicament.

Conveniently this is a compound of formula (I), or a pharmaceutically acceptable salt or an in vivo hydrolysable ester thereof, for use as a medicament for producing an elevation of PDH activity in a warm-blooded animal such as a human being.

Particularly this is a compound of formula (I), or a pharmaceutically acceptable salt or an in vivo hydrolysable ester thereof, for use as a medicament for treating diabetes mellitus in a warm-blooded animal such as a human being.

In another aspect of the invention, particularly this is a compound of formula (I), or a pharmaceutically acceptable salt or an in vivo hydrolysable ester thereof, for use as a medicament for treating diabetes mellitus, peripheral vascular disease and myocardial ischaemia in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the production of an elevation of PDH activity in a warm-blooded animal such as a human being Thus according to a further aspect of the invention there is provided the use of a compound of the formula (I), or a pharmaceutically acceptable salt or an in vivo hydrolysable ester thereof in the manufacture of a medicament for use in the treatment of diabetes mellitus in a warm-blooded animal such as a human being.

Thus according to a further aspect of the invention there is provided the use of a compound of the formula (I), or a pharmaceutically acceptable salt or an in Vivo hydrolysable ester thereof in the manufacture of a medicament for use in the treatment of diabetes mellitus, peripheral vascular disease and myocardial ischaemia in a warm-blooded animal such as a human being.

According to a further feature of the invention there is provided a method for producing an elevation of PDH activity in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus, peripheral vascular disease and myocardial ischaemia in a warm-blooded animal, such as a human being, in need of such treatment which comprises administering to said animal an effective amount of a compound of formula (I) or a pharmaceutically acceptable salt or an its vivo hydrolysable ester thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed.However the daily dose will necessarily be varied depending upon the host treated the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment:

i) insulin;
ii) insulin secretagogue agents designed to stimulate insulin secretion (for example glibenclamide, tolbutamide, other sulphonylureas);
iii) oral hypoglycaemic agents such as metformin, thiazolidinediones;
iv) agents designed to reduce the absorption of glucose from the intestine (for example acarbose);
v) agents designed to treat complications of prolonged hyperglycaemia;
vi) other agents used to treat lactic acidaemia;
vii) inhibitors of fatty acid oxidation;
viii) lipid lowering agents;
ix) agents used to treat coronary heart disease and peripheral vascular disease such as aspirin, pentoxifylline, cilostazol; and/or
x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimers disease and/or atherosclerosis. Alternatively such compounds of the invention may be useful in a range of disease states including peripheral vascular disease, (including intermittent claudication), cardiac failure and certain cardiac myopathies, myocardial ischaemia, cerebral ischaemia and reperfusion, muscle weakness, hyperlipidaemias, Alzheimers disease and/or atherosclerosis in particular peripheral vascular disease and myocardial ischaemia.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent was carried out using a rotary evaporator under reduced pressure (600–4000 Pascals; 4.5–30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI"

(iv) in general, the course of reactions was followed by TLC and reaction times are given for illustration only;

(v) yields are given for illustration only and are not necessarily those which can be obtained by diligent process development; preparations were repeated if more material was required; (vi) when given, ¹H NMR data is quoted and is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the negative mass ion —(M—H)⁻;

(x) the following abbreviations are used:
DMSO dimethyl sulphoxide;
DMF N-dimethylformamide;
DCM dichloromethane; and
EtOAc ethyl acetate; and (xi) where a Chem Elut column is referred to, this means a "Hydromatrix" extraction cartridge for adsorption of aqueous material, i.e. a polypropylene tube containing a special grade of flux-calcined, high purity, inert diatomaceous earth, pre-buffered to pH 4.5 or 9.0, incorporating a phase-separation filtering material, used according to the manufacturers instructions, obtained from Varian, Harbor City, Calif., USA under the name of "Extube, Chem Elut"; "Extube" is a registered trademark of International Sorbent Technology Limited;

(xii) where (R) or (S) stereochemistry is quoted at the beginning of a name, unless further clarified, it is to be understood that the indicated stereochemistry refers to the NH—C(O)—C*(OH)(R³)(R⁴) centre as depicted in formula (I).

EXAMPLE 1

(R)-N-[2,3-Dichloro-4-((R,S)-2-hydroxypropylaminosulphonyl)phenyl]-3,3,3-trifluoro-2-hydroxy-2-methylpropanamide To a stirred solution of(R,S)-1-amino-2-propanol (93 mg, 1.25 mmol) in EtOAc (10 ml) was added a solution of (R)-N-[2,3-dichloro-4-(chlorosulphonyl)phenyl]-3,3,3-trifluoro-2-hydroxy-2-methylpropanamide (200 mg, 0.5 mmol) (Method 1) in EtOAc (10 ml). The resultant mixture was stirred at ambient temperature overnight, washed with 1 M aqueous hydrochloric acid, saturated sodium hydrogen carbonate solution and brine, dried and evaporated to give the title compound as a foam (100 mg, 0.23 mmol); NMR: 1.05 (d, 3H), 1.7 (s, 3H), 2.8 (m, 2H), 3.65 (m, 1H), 4.7 (d, 1H), 8.05 (d, 1H), 8.25 (d, 1H); m/z 437.

EXAMPLE 2

(R)-N-[2-Chloro-3-methyl-4-((S)-2-hydroxypropylamino-sulphonyl)phenyl]-3,3,3-trifluoro-2-hydroxy-2-methylpropanamide The title compound was prepared by the procedure of Example 1 except (S)-(+)-1-amino-2-propanol was used in place of (R,S) 1-amino-2-propanol. NMR: 0.98 (d, 3H), 1.62 (s, 3H), 2.7–2.85 (m, 2H), 3.5–3.6 (m, 1H), 4.7 (d, 1H), 7.93 (s, 1H), 7.95 (s, 1H), 7.85 (d, 1H), 8.2 (d, 1H), 10.0 (brs, 1H); m/z 437.

EXAMPLE 3

(R)-N-[2,3-Dichloro-4-(4-hydroxypiperidin-1-ylsulphonyl)phenyl]-3,3,3-trifluoro-2-hydroxy-2-methylpropanamide To a stirred solution of 4-hydroxypiperidine (126 mg, 1.25 mmol) in EtOAc (10 ml) was added a solution of (R)-N-[2,3-dichloro-4-(chlorosulphonyl)phenyl]-3,3,3-trichluoro-2-hydroxy-2-methylpropanamide (200 mg, 0.5 mmol) (Method 1) in EtOAc (10 ml). The resultant mixture was stirred at ambient temperature overnight, washed with 1 M aqueous hydrochloric acid, saturated sodium hydrogen carbonate solution and brine, dried and evaporated to give the title compound as a foam (77 mg, 0.17 mmol); NMR: 1.4 (m, 2H), 1.6 (s, 3H), 1.7 (m, 2H), 3.0 (m, 2H), 3.4 (m, 2H), 3.6 (m, 1H), 4.75 (d, 1H), 8.0 (d, 1H), 8.3 (d, 1H); m/z 463.

EXAMPLE 4

(R)-N-[2,3-Dichloro-4-(4-methoxyanilinosulphonyl)phenyl]-3,3,3-trifluoro-2-hydroxy-2-methylpropanamide To a stirred solution of p-anisidine (74 mg, 0.6 mmol), pyridine (0.14 ml, 1.0 mmol) and 4-dimethylaminopyridine (10 mg) in EtOAc (10 ml) was added a solution of (R)-N-[2,3-dichloro-4-(chlorosulphonyl)phenyl]-3,3,3-trifluoro-2-hydroxy-2-methylpropanamide (200 mg, 0.5 mmol) (Method 1) in EtOAc (10 ml). The resultant mixture was stirred at ambient temperature overnight, washed with 1 M aqueous hydrochloric acid, saturated sodium hydrogen carbonate solution and brine, dried and evaporated. The residue was chromatographed on a Bond Elut column (using 10% EtOAc in DCM as eluent) to give the title compound as a foam (114 mg, 0.23 mmol); NMR: 1.6 (s, 3H), 3.6 (s, 3H), 6.8 (d, 2H), 7.0 (d, 2H), 7.95 (d, 1H), 8.1 (d, 1H); m/z 485.

EXAMPLE 5

(R)-N-[2,3-Dichloro-4-(5-methylpyrid-2-ylaminosulphonyl)phenyl]-3,3,3-trifluoro-2-hydroxy-2-methylpropanamide A mixture of (R)-N-(2,3-dichloro-4-chlorosulphonylphenyl)-3,3,3-trifluoro-2-hydroxy-2-methylpropanamide (200 mg, 0.5 mmol) (Method 1) and 2-amino-5-methylpyridine (81 mg, 0.80 mmol) in pyridine (5 ml) was stirred at 80° C. overnight. The mixture was cooled to ambient temperature, poured onto water (50 ml) and extracted with EtOAc (2×25 ml). The organic layer was separated, washed with 1 M aqueous hydrochloric acid, saturated sodium hydrogen carbonate solution, brine, dried and evaporated to give the title compound as a solid (40 mg, 0.08 mmol); NMR: 1.6 (s, 3H), 2.1 (s, 3H), 7.1 (d, 1H), 7.6 (d, 1H), 7.75 (s, 1H), 8.1 (s, 2H); m/z 470.

EXAMPLE 6

(R)-N-(4-[Anilinosulphonyl]-2,5-dimethoxyphenyl)-3,3,3-trifluoro-2-hydroxy-2-methylpropanamide Oxalyl chloride (0.13 ml, 1.5 mmol) was added to a stirred suspension of (R)-(+)-2-hydroxy-2-methyl-3,3,3-trifluoropropanoic acid (0.154 g, 0.97 mmol) (Method 3) in DCM (10 ml) containing DMF (1 drop). The mixture was stirred at ambient temperature overnight, then 4-[anilinosulphonyl]-2,5-dimethoxyaniline (200 mg, 0.65 mmol)† and 2,6-di-t-butylpyridine (0.14 ml, 0.66 mmol) was added and the resulting mixture stirred a further 2 hours at room temperature. Dichloromethane (25 ml) was added and the mixture was washed with water (2×50 ml) and brine then dried. Volatile material was removed by evaporation and the residue was purified by chromatography on a silica gel Mega Bond Elut column eluting with 50% EtOAc/iso-hexane to give the title compound as a solid (0.125 g, 0.28 mmol); M.p: 194–195° C., NMR: 1.7 (s, 3H), 3.8 (s, 3H), 4.1 (s, 3H), 6.9 (s, 1H), 7.05 (m, 3H), 7.2 (m, 3H), 8.3 (s, 1H), 9.1 (brs, 1H); m/z 447.

† This compound was reported in "Manufacture of C.I. Pigment Yellow 97", Jauer, E. A., Groth, K. R., Dorst, H., Freitag, R. and Kluge, S., PI DD298254-A5 (German patent), 1992.

EXAMPLE 7

(R)-N-(2,5-Dimethoxy-4-[dimethylaminosulphonyl] phenyl)-3,3,3-trifluoro-2-hydroxy-2-methylpropanamide Oxalyl chloride (0.15 ml, 1.8 mmol) was added to a stirred suspension of (R)-(+)-2-hydroxy-2-methyl-3,3,3-trifluoropropanoic acid (0.18 g, 1.15 mmol) (Method 3) in DCM (10 ml) containing DMF (1 drop). The mixture was stirred at ambient temperature overnight, then 2,5-dimethoxy-4-[dimethylaminosulphonyl]aniline (200 mg, 0.77 mmol)‡ and 2,6-di-t-butylpyridine (0.19 ml, 0.9 mmol) was added and the resulting mixture stirred a further 2 hours at room temperature. Dichloromethane (25 ml) was added and the mixture was washed with water (2×50 ml) and brine then dried. Volatile material was removed by evaporation and the residue was purified by chromatography on a silica gel Mega Bond Elut column eluting with 50% EtOAc/iso-hexane to give the title compound as a foam (212 mg, 0.53 mmol); NMR: 1.74 (s, 3H), 2.83 (s, 6H), 3.91 (s, 6H), 7.40 (s, 1H), 8.27 (s, 1H), 9.17 (s, 1H); m/z 399.

‡ This compound was reported in "Synthesis and application of some sulphonamido acid azo dyes and sulphonamido direct azo dyes", Sebe, I. and Clopotar, M., Rev. Roum. Chim., 1993, 38(9), 1083–9.

EXAMPLE 8

(R)-N-[2,3-Dichloro-4-(methylaminosulphonyl) phenyl]-3,3,3-trifluoro-2-hydroxy-2-methylpropanamide To a stirred solution of methylamine (2.0 M in methanol, 0.42 ml, 0.83 mmol) in DCM(15 ml) was added a solution of(R)-N-[2,3-dichloro-4-(chlorosulphonyl) phenyl]-3,3,3-trifluoro-2-hydroxy-2-methylpropanamide (Method 1, 150 mg, 0.38 mmol) in DCM (10 ml). The resultant mixture was stirred at ambient temperature overnight and then washed with saturated sodium hydrogen carbonate solution and brine, dried and evaporated. The residue was purified by column chromatography using EtOAc as eluent to give the title compound as a foam (86 mg, 0.22 mmol). NMR: 1.6 (s, 3H), 2.45 (d, 3H), 7.8 (q, 1H), 7.95 (d, 1H), 8.0 (s, 1H), 8.2 (d, 1H) and 9.95 (brs, 1H); m/z 393.

EXAMPLES 9–25

The procedure described in Example 8 was repeated using the appropriate amine to replace the methylamine using EtOAc as solvent to obtain the compounds described below.

| Ex | Compound | m/z | NMR |
|---|---|---|---|
| 9 | (R)-N-{2,3-Dichloro-4-[(morpholino)sulphonyl] phenyl}-3,3,3-trifluoro-2-hydroxy-2-methylpropanamide | 449 | 1.6(s, 3H), 3.2(t, 4H), 3.6(t, 4H), 8.05(d, 1H), 8.1(s, 1H), 8.3(d, 1H), 10.0(s, 1H) |
| 10 | (R)-N-{2,3-Dichloro-4-[(isopropylamino) sulphonyl]phenyl}-3,3,3-trifluoro-2-hydroxy-2-methylpropanamide | 421 | 1.0(d, 6H), 1.6(s, 3H), 7.9–8.05(m, 3H), 8.2(d, 1H), 9.95(brs, 1H) |
| 11 | (R)-N-[2,3-Dichloro-4-(aminosulphonyl) phenyl]-3,3,3-trifluoro-2-hydroxy-2-methylpropanamide | 379 | 1.6(s, 3H), 7.75(s, 2H), 7.95 (s, 1H), 8.0(d, 1H), 8.1(d, 1H), 9.95(s, 1H) |
| 12 | (R)-N-[2,3-Dichloro-4-(dimethylamino-sulphonyl)phenyl]-3,3,3-trifluoro-2-hydroxy-2-methylpropanamide | 407 | 1.6(s, 3H), 2.8(s, 6H), 8.0 (d, 1H), 8.05(brs, 1H), 8.25 (d, 1H), 9.95(brs, 1H) |
| 13 | (R)-N-{2,3-Dichloro-4-[(1,1-dimethyl-2-hydroxyethylamino)sulphonyl]phenyl}-3,3,3-trifluoro-2-hydroxy-2-methylpropanamide | 451 | 1.05(s, 6H), 1.6(s, 3H), 7.45 (s, 1H), 8.0(brs, 1H), 8.05(d, 1H), 8.2(d, 1H), 9.95(s, 1H) |
| 14 | (R)-N-{2,3-Dichloro-4-[(pyrid-3-ylamino) sulphonyl]phenyl}-3,3,3-trifluoro-2-hydroxy-2-methylpropanamide | 456 | 1.6(s, 3H), 7.3(m, 1H), 7.5 (m, 1H), 8.0(s, 1H), 8.1(d, 1H), 8.2(s, 1H), 8.25(dd, 1H), 8.3(d, 1H), 9.95(s, 1H). |
| 15 | (R)-N-{2,3-Dichloro-4-[(4-acetamidoanilino) sulphonyl]phenyl}-3,3,3-trifluoro-2-hydroxy-2-methylpropanamide | 512 | 1.6(s, 3H), 1.95(s, 3H), 7.0 (d, 2H), 7.4(d, 2H), 7.9–8.05 (m, 2H), 9.8(s, 1H), 9.9(brs, 1H) |

| Ex | Compound | m/z |
|---|---|---|
| 16 | (R)-N-{2,3-Dichloro-4-[(2-hydroxyethylamino)sulphonyl]phenyl}-3,3,3-trifluoro-2-hydroxy-2-methylpropanamide | 423 |
| 17 | (R)-N-[2,3-Dichloro-4-(ethylaminosulphonyl)phenyl]-3,3,3-trifluoro-2-hydroxy-2-methylpropanamide | 407 |
| 18 | (R)-N-(2,3-Dichloro-4-{[N',N'-bis-(2-hydroxyethyl)amino]sulphonyl}phenyl)-3,3,3-trifluoro-2-hydroxy-2-methylpropanamide | 467 |

| | | |
|---|---|---|
| | -continued | |
| 19 | (R)-N-{2,3-Dichloro-4-[(3-hydroxypyrrolidin-1-yl)sulphonyl]phenyl}-3,3,3-trifluoro-2-hydroxy-2-methylpropanamide | 449 |
| 20 | (R)-N-{2,3-Dichloro-4-[(3-hydroxypiperidin-1-yl)sulphonyl]phenyl}-3,3,3-trifluoro-2-hydroxy-2-methylpropanamide | 463 |
| 21 | (R)-N-{2,3-Dichloro-4-[(1-methyl-2-hydroxyethylamino)sulphonyl]phenyl}-3,3,3-trifluoro-2-hydroxy-2-methylpropanamide | 437 |
| 22 | (R)-N-{2,3-Dichloro-4-[(4-hydroxycyclohexylamino)sulphonyl]phenyl}-3,3,3-trifluoro-2-hydroxy-2-methylpropanamide | 477 |
| 23 | (R)-N-{2,3-Dichloro-4-[(2,3-dihydroxypropylamino)sulphonyl]phenyl}-3,3,3-trifluoro-2-hydroxy-2-methylpropanamide | 453 |
| 24 | (R)-N-{2,3-Dichloro-4-[(4-acetylanilino)sulphonyl]phenyl}-3,3,3-trifluoro-2-hydroxy-2-methylpropanamide | 497 |
| 25 | (R)-N-{2,3-Dichloro-4-[(4-dimethylaminoanilino)sulphonyl]phenyl}-3,3,3-trifluoro-2-hydroxy-2-methylpropanamide | 498 |

EXAMPLE 26

(R)-N-[2-Chloro-3-methyl-4-((R,S)-2-hydroxypropylaminosulphonyl)phenyl]-3,3,3-trifluoro-2-hydroxy-2-methylpropanamide A solution of (R,S)-1-amino-2-propanol (180 mg, 2.4 mmol) in EtOAc (20 ml) was added to a stirred solution of (R)-N-[2-chloro-3-methyl-4-(chlorosulphonyl)phenyl]-3,3,3-trifluoro-2-hydroxy-2-methylpropanamide (Method 4; 400 mg, 1.1 mmol) in EtOAc (20 ml). The resultant mixture was stirred at ambient temperature overnight, washed with 1 M aqueous hydrochloric acid, saturated aqueous sodium hydrogen carbonate solution and brine, dried and evaporated to dryness. The residue was purified by column chromatography using EtOAc as eluent to give the title compound as a foam (260 mg, 0.62 mmol). NMR: 0.95 (d, 3H), 1.6 (s, 3H), 2.65 (s, 3H), 2.70 (m, 2H), 3.55 (m, 1H), 4.6 (d, 1H), 7.8 (t, 1H), 7.85 (d, 1H), 8.0 (s, 1H), 8.15 (d, 1H), 9.9 (s, 1H); m/z 417.

EXAMPLES 27–30

The procedure described in Example 26 was repeated using the appropriate amine to replace the (R,S)-1-amino-2-propanol using EtOAc as solvent to obtain the compounds described below.

EXAMPLE 31

(R)-N-[2,3-Dichloro-4-(2-methoxypyrid-5-ylaminosulphonyl)phenyl]-3,3,3-trifluoro-2-hydroxy-2-methylpropanamide A solution of (R)-N-(2,3-Dichloro-4-chlorosulphonylphenyl)-3,3,3-trifluoro-2-hydroxy-2-methylpropanamide (Method 1; 0.3 mmol) and pyridine (0.33 mmol) in DCM (5 ml) was added to a solution of 5-amino-2-methoxypyridine (0.3 mmol) in DCM (2 ml). The resultant mixture was stirred at ambient temperature overnight. The DCM was evaporated and resulting mixture was partitioned between EtOAc (5 ml) and 1 M HCl (4 ml), the EtOAc layer was separated and washed with saturated aqueous sodium hydrogen carbonate solution and brine then dried and evaporated to give the title compound as a gum (50 mg). M/z 486.

EXAMPLES 32–37

The following examples were prepared by the procedure of Example 31 using the appropriate amine to replace the 5-amino-2-methoxypyridine.

| Ex | Compound | NMR | m/z |
|---|---|---|---|
| 27 | (R)-N-{2-Chloro-3-methyl-4-[(3-hydroxyprop-2-ylamino)sulphonyl]phenyl}-3,3,3-trifluoro-2-hydroxy-2-methylpropanamide | 0.9(d, 3H), 1.6(s, 3H), 2.6(s, 3H), 3.05(m, 1H), 7.7(d, 1H), 7.9 (d, 1H), 8.0(s, 1H), 8.1(d, 1H), 9.85(s, 1H) | 417 |
| 28 | (R)-N-{2-Chloro-3-methyl-4-[(4-hydroxypiperidin-1-yl)sulphonyl]phenyl}-3,3,3-trifluoro-2-hydroxy-2-methylpropanamide | 1.4(m, 2H), 1.6(s, 3H), 1.75(m, 2H), 2.6(s, 3H), 2.9(m, 2H), 2.6 (m, 1H), 4.7(d, 1H), 7.85(d, 1H), 8.0(s, 1H), 8.2(d, 1H) | 443 |
| 29 | (R)-N-{2-Chloro-3-methyl-4-[((R,S)-2,3-dihydroxypropyl-amino)sulphonyl]phenyl}-3,3,3-trifluoro-2-hydroxy-2-methylpropanamide | 1.6(s, 3H), 2.6(m, 4H), 2.9(m, 1H), 2.25(m, 2H), 2.4(m, 1H), 4.45(t, 1H), 4.7(d, 1H), 7.7(t, 1H), 7.85(d, 1H), 8.0(s, 1H), 8.15 (d, 1H), 9.85(s, 1H) | 433 |
| 30 | (R)-N-{2-Chloro-3-methyl-4-[(3-hydroxypyrrolidin-1-yl)sulphonyl]phenyl}-3,3,3-trifluoro-2-hydroxy-2-methylpropanamide | 1.6(s, 3H), 1.8(m, 1H), 1.95(m, 1H), 2.65(s, 3H), 3.1(d, 1H), 3.3 (m, 3H), 4.25(s, 1H), 5.05(s, 1H), 7.85(d, 1H), 8.0(s, 1H), 8.2(d, 1H), (s, 1H) | 429 |

| Ex | Compound | M/z |
|---|---|---|
| 32 | (R)-N-[2,3-Dichloro-4-(4-methylanilinosulphonyl)phenyl]-3,3,3-trifluoro-2-hydroxy-2-methylpropanamide | 469 |
| 33 | (R)-N-[2,3-Dichloro-4-(N-methylanilinosulphonyl)phenyl]-3,3,3-trifluoro-2-hydroxy-2-methylpropanamide | 469 |
| 34 | (R)-N-[2,3-Dichloro-4-(2,4-dimethoxyanilinosulphonyl)-phenyl]-3,3,3-trifluoro-2-hydroxy-2-methylpropanamide | 515 |
| 35 | (R)-N-[2,3-Dichloro-4-(3,4-dimethoxyanilinosulphonyl)-phenyl]-3,3,3-trifluoro-2-hydroxy-2-methylpropanamide | 515 |
| 36 | (R)-N-[2,3-Dichloro-4-(anilinosulphonyl)phenyl]-3,3,3-trifluoro-2-hydroxy-2-methylpropanamide | 455 |
| 37 | (R)-N-[2,3-Dichloro-4-(2-methoxyanilinosulphonyl)phenyl]-3,3,3-trifluoro-2-hydroxy-2-methylpropanamide | 485 |

EXAMPLES 38–43

The following procedure was used to prepare Examples 38–43.

(R)-N-[2-Chloro-3-methyl-4-(chlorosulphonyl)phenyl]-3,3,3-trifluoro-2-hydroxy-2-methylpropanamide (Method 4; 1.15 g) or (R)-N-(2,3-dichloro-4-chlorosulphonylphenyl)-3,3,3-trifluoro-2-hydroxy-2-methylpropanamide (Method 1; 1.59 g) in EtOAc (50 ml) was added dropwise to a solution of the appropriate aminoalcohol (0.682 g) in EtOAc (50 ml) over 5 minutes. The reaction mixture was left to stir at ambient temperature overnight under an argon atmosphere. The reaction was washed with aqueous HCl (1M, 3×100 ml) and the EtOAc extracts were combined, dried and the volatiles removed by evaporation. The residue was chromatographed on a Bond Elut column eluting with 50% EtOAc/isohexane to afford the product as a white solid in typically 75% yield.

EXAMPLE 44

(R)-N-{2-Chloro-3-methylsulphonyl)-4-[(R,S)-2-hydroxypropylaminosulphonyl]phenyl}-3,3,3-trifluoro-2-hydroxy-2-methylpropanamide To a stirred solution of sodium methanethiolate (25.2mg, 0.36mmol) in DMA (5 ml) under argon, was added a solution of (R)-N- {2-chloro-3-iodo-4-[(R,S)-2-hydroxypropylaminosulphonyl]phenyl }-3,3,3-trifluoro-2-hydroxy-2-methylpropanamide (Example 45; 150 mg, 0.3 mmol) in DMA (2 ml) followed by copper (I) chloride (12 mg, 0.12 mmol). The mixture was heated to 150° C. and stirred at this temperature for 24 hours. EtOAc (150 ml) was added followed by water (100 ml) and the resulting suspension was filtered through diatomaceous earth which was washed with EtOAc (100 ml). The layers were separated and the organic layer washed with brine (3×100 ml) and dried. The crude organic layer was concentrated under reduced pressure and purified by flash column chromatography, on silica using 10%–30% EtOAc in isohexane as the eluent to give the title compound (12 mg, 10%) as a colourless gum. NMR: 1.0 (d, 3H), 1.6 (s, 3H), 2.75 (m, 2H), 3.6 (m, 1H), 4.7 (d, 1H), 7.25 (dd, 1H), 7.95 (m, 2H), 8.25 (d, 1H), 9.9 (s, 1H); m/z: 449.

EXAMPLE 45

(R)-N-{2-Chloro-3-iodo-4-[(R,S)-2-hydroxypropylaminosulphonyl]phenyl}-3,3,3-trifluoro-2-hydroxy-2-methlylpropanamide To a stirred solution of (R)-N-[4-chlorosulphonyl-3-iodo-2-chlorophenyl]-2-hydroxy-2-methyl-3,3,3-trifluoropropanamide (Method 6; 200 mg, 0.41 mmol) in EtOAc (10 ml) was added a solution of 1-amino-2-propanol (0.11 g, 1.2 mmol) in EtOAc (10 ml). The mixture was stirred for 20 hours at room temperature. After this time, the

| Ex | Compound | NMR | M/z | SM |
|---|---|---|---|---|
| 38 | (R)-N-[2-Chloro-3-methyl-4-((S)-3-hydroxyprop-2-ylaminosulphonyl)phenyl]-3,3,3-trifluoro-2-hydroxy-2-methylpropanamide | 0.95(d, 3H), 1.6(s, 3H), 2.65(s, 3H), 3.0–3.15(m, 2H), 3.2–3.3 (m, 1H), 4.65(dd, 1H), 7.7(d, 1H), 7.9(d, 1H), 8.0(s, 1H), 8.15(d, 1H), 9.9(s, 1H) | 417 | (S)-(+)-2-amino-propanol |
| 39 | (R)-N-[2-Chloro-3-methyl-4-((R)-3-hydroxyprop-2-ylaminosulphonyl)phenyl]-3,3,3-trifluoro-2-hydroxy-2-methylpropanamide | 0.90(d, 3H), 1.6(s, 3H), 2.65(s, 3H), 3.0-3.15(m, 2H), 3.2–3.3 (m, 1H), 4.65(dd, 1H), 7.7(d, 1H), 7.9(d, 1H), 8.0(s, 1H), 8.15(d, 1H), 9.9(s, 1H) | 417 | (R)-(−)-2-amino-propanol |
| 40 | (R)-N-[2-Chloro-3-methyl-4-((S)-2-hydroxypropylamino-sulphonyl)phenyl]-3,3,3-trifluoro-2-hydroxy-2-methylpropanamide | 0.95(d, 3H), 1.6(s, 3H), 2.65(s, 3H), 2.65–2.75(m, 2H), 3.5–3.6 (m, 1H), 4.65(dd, 1H), 7.8(s, 1H), 7.85(d, 1H), 8.0(s, 1H), 8.15(d, 1H), 9.9(s, 1H) | 417 | (S)-(+)-2-hydroxy-propyl-amine |
| 41 | (R)-N-[2-Chloro-3-methyl-4-((R)-2-hydroxypropylamino-sulphonyl)phenyl]-3,3,3-trifluoro-2-hydroxy-2-methylpropanamide | 0.95(d, 3H), 1.6(s, 3H), 2.65(s, 3H), 2.65–2.75(m, 2H), 3.5–3.6 (m, 1H), 4.60(dd, 1H), 7.8(s, 1H), 7.85(d, 1H), 8.0(s, 1H), 8.15(d, 1H), 9.9(s, 1H) | 417 | (R)-(−)-2-hydroxy-propyl-amine |
| 42 | (R)-N-[2,3-Dichloro-4-((R)-3-hydroxyprop-2-ylamino-sulphonyl)phenyl]-3,3,3-trifluoro-2-hydroxy-2-methylpropanamide | 0.97(d, 3H), 1.64(s, 3H), 3.14 (m, 2H), 3.3(m, 1H), 4.7(t, 1H), 7.89(d, 1H), 8.03(brs, 1H), 8.07 (d, 1H), 8.2(d, 1H), 10.0(brs, 1H) | 437 | (R)-(−)-2-amino-propanol |
| 43 | (R)-N-[2,3-Dichloro-4-((S)-3-hydroxyprop-2-ylamino-sulphonyl)phenyl]-3,3,3-trifluoro-2-hydroxy-2-methylpropanamide | 0.97(d, 3H), 1.64(s, 3H), 3.14 (m, 2H), 3.3(m, 1H), 4.7(t, 1H), 7.89(d, 1H), 8.03(brs, 1H), 8.07 (d, 1H), 8.2(d, 1H), 10.0(brs, 1H) | 437 | (S)-(+)-2-amino-propanol | reaction mixture was washed with 1M hydrochloric acid solution and saturated sodium hydrogen carbonate solution. The aqueous layers were removed using a Chem Elut column. The crude organic extracts were concentrated under reduced pressure, then chromatographed on a 20 g silica Bond Elut column using 20% EtOAc in isohexane as the eluent to give the title compound (165 mg, 74%). NMR: 1.0 (d, 3H), 1.6 (s, 3H), 2.8 (dd, 2H), 3.6 (m, 1H), 4.7 (d, 1H), 7.6 (m, 1H), 8.0 (d, 2H), 8.25 (d, 1H), 9.9 (s, 1H); m/z 529.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

(R)-N-(2,3-Dichloro-4-chlorosulphonylphenyl)-3,3,3-trifluoro-2-hydroxy-2-methylpropanamide (R)-N-(2,3-Dichlorophenyl)-3,3,3-trifluoro-2-hydroxy-2-methylpropanamide (1.0 g, 3,3 mmol) (Method 2) was added portion wise to a cooled (ice bath) and stirred solution of chlorosulphonic acid (5 ml). The resulting mixture was heated to 85° C. for 270 mins. The reaction mixture was then cooled to room temperature and poured onto an ice/water slurry. The resulting aqueous mixture was extracted with DCM twice. The combined organic extracts were washed with brine, dried and were concentrated to yield an oil. Purification by column chromatography (10–20% EtOAc/iso-hexane) yielded the title compound as a solid (0.80 g, 2.0 mmol). NMR (CDCl$_3$): 1.75 (s, 3H), 3.65 (s, 1H), 8.05 (d, 1H), 8.60 (d, 1H), 9.50 (s, 1H); MS: 398, 400.

Method 2

(R)-N-(2,3-Dichlorophenyl-3,3,3-trifluoro-2-hydroxy-2-methylpropanamide 2,3-Dichloroaniline (2 g, 12.3 mmol) and 2,6-di-t-butylpyridine (3 ml) were added to a solution of (S)-3,3,3,-trifluoro-2-hydroxy-2-methylpropanoyl chloride [produced in situ by reaction of (R)-3,3,3,-trifluoro-2-hydroxy-2-methylpropanoic acid (1.95 g, 12.3 mmol) (Method 3) with oxalyl chloride (1.2 ml, 13.5 mmol) and DMF (one drop) for 6 h at room temperature] in DCM. The resulting solution was stirred for 16h at room temperature. The reaction mixture was then concentrated and purified by column chromatography (10–20% EtOAc/iso-hexane) to yield an oil, which was recrystallized (DCM/iso-hexane) to give the title compound as a white solid (1.7 g, 5.6 mmol). NMR (CDCl$_3$): 1.80 (s, 3H), 3.5 (s, 1H), 7.25 (m, 2H), 8.3 (dd, 1H), 9.00 (s, 1H); MS: 300, 302.

Method 3

(R)-(+)-2-Hydroxy-2-methyl-3,3,3-trifluoropropanoic Acid (R,S)-2-Hydroxy-2-methyl-3,3,3-trifluoropropanoic acid was resolved according to the resolution method described in European Patent Application No. EP 524781 (described for the preparation of the (S)-(–)-acid) except that (1S,2R)-norephedrine was used in place of (1R, 2S)-norephedrine or (S)-(–)-1-phenylethylamine to yield the title compound, [α]$_D^{20}$+18.1° (c, 8.8 in MeOH); NMR analysis of the acid in the presence of (R)-(+)-1-phenylethylamine gave an enantiomerical purity of >98%. NMR (CDCl$_3$): 1.27 (s, 3H) for the (R)-enantiomer, 1.21 (s, 3H) for the (S)-enantiomer.

Method 4

(R)-N-[2-Chloro-3-methyl-4-(chlorosulphonyl)phenyl]-3,3,3-trifluoro-2-hydroxy-2-methylpropanamide (R)-N-{2-chloro-3-methylphenyl}-3,3,3-trifluoro-2-hydroxy-2-methylpropanamide (Method 5; 5.0 g, 17.8 mmol) was added in portions to cooled (0° C.) chlorosulphonic acid (5.8 ml) over 15 mins and then the mixture was heated to 85° C. After 4.5 h the reaction mixture was cooled in an ice bath and then poured very slowly onto a stirred ice-water mixture (70 ml). The mixture was extracted with DCM (2×75 ml), the combined organic layers were washed with brine, dried and evaporated. The residue was chromatographed on silica with 20% EtOAc/hexane as eluent to give the title compound as a solid (2.5 g, 6.6 mmol). NMR (CDCl$_3$): 1.8 (s, 3H), 3.45 (s, 1H), 3.85 (s, 3H), 8.05 (d, 1H), 8.55 (d, 1H), 8.55 (brs, 1H); m/z 378.

Method 5

(R)-N-{2-Chloro-3-methylphenyl}-3,3,3-trifluoro-2-hydroxy-2-methylpropanamide

A solution of (S)-3,3,3-trifluoro-2-trimethylsilyoxy-2-methylpropanoyl chloride (prepared from (R)-(+)-2-Hydroxy-2-methyl-3,3,3-trifluoropropanoic acid (Method 3) as described in J Med. Chem., 1999, 42, 2741–2746)(17.4 g, 70 mmol) in DCM (50 ml) was added to a stirred mixture of 2-chloro-3-methyl-aniline (WO 9741846; 8.25 g, 141.6 mmol) and pyridine (7.1 ml, 87.5 mmol) in DCM (100 ml). The resultant mixture was stirred at ambient temperature for 24 hours, washed with 1 M hydrochloric acid, saturated sodium hydrogen carbonate solution and brine, dried and evaporated. The residue was dissolved in methanol (150 ml), treated with 2 M hydrochloric acid (130 ml) and the mixture stirred at ambient temperature for 18 hour. The methanol was evaporated, the aqueous layer was extracted with EtOAc (2×75 ml), the EtOAc extracts were combined and washed with saturated sodium hydrogen carbonate solution and brine, dried and evaporated. The residue was chromatographed on silica with DCM as eluent to give the title compound as a solid (13.6 g, 48.4 mmol). NMR (CDCl$_3$): 1.75 (s, 3H), 2.4 (s, 3H), 3.75 (s, 1H), 7.05 (d, 1H), 7.2 (dd, 1H), 8.2 (d, 1H), 8.85 (brs, 1H); m/z 280.

Method 6

(R)-N-[4-Chlorosulphonyl-3-iodo-2-chlorophenyl]-2-hydroxy-2-methyl-3,3,3-trifluoropropanamide (R)-N-[3-Iodo-2-chlorophenyl]-2-hydroxy-2-methyl-3,3,3-trifluoropropanamide (Method 7) (4.92 g) was added in portions to chlorosulphonic acid (18 ml) at 0° C. The reaction mixture was heated to 80° C. for 4 hours, allowed to cool to ambient temperature and poured onto ice-water (200 g). The mixture was extracted into DCM (2×250 ml), the organic phase was washed with brine (300 ml) and dried. Volatile material was removed by evaporation to give the title compound (4.8 g) as a brown gum. NMR (CDCl$_3$) 1.78 (s, 3H), 3.59 (s, 1H), 8.23 (d, 1H), 8.74 (d, 1H), 9.53 (s, 1H); m/z: 490.

Method 7

(R)-N-[3-Iodo-2-chlorophenyl]-2-hydroxy-2-methyl-3,3,3-trifluoropropanamide

To a cooled solution of (R)-N-[3-amino-2-chlorophenyl]-2-hydroxy-2-methyl-3,3,3-trifluoropropanamide (Method 8)

(12.5 g) in concentrated sulphuric acid (25 ml) and water (70 ml) was added a solution of sodium nitrite (3.15 g) in water (70 ml) dropwise. The reaction mixture was allowed to stir for 10 minutes and for 1 hour at ambient temperature. A solution of potassium iodide (22.2 g) in water (70 ml) was added cautiously and the mixture was heated to 100° C. for 2.5 hours. The reaction mixture was allowed to cool to ambient temperature, EtOAc (500 ml) was added and the organic phase was washed with brine (300 ml) and dried. Volatile material was removed by evaporation and the residue was purified by flash column chromatography eluting with 5–20% EtOAc/isohexane to give the title compound (13.5 g) as a cream solid. NMR (CDCl$_3$) 1.76 (s, 3H), 3.63 (s, 1H), 7.05 (t, 1H), 7.68 (d, 1H), 8.36 (d, 1H), 8.97 (brs, 1H); m/z: 392.

Method 8

(R)-N-[3-Amino-2-chlorophenyl]-2-hydroxy-2-methyl-3,3,3-trifluoropropanamide

To a stirred solution of (R)-N-[3-nitro-2-chlorophenyl]-2-hydroxy-2-methyl-3,3,3-trifluoropropanamide (Method 9) (14.3 g) in EtOAc (250 ml) under a hydrogen atmosphere was added 10% palladium on carbon (1.6 g). The reaction mixture was allowed to stir at room temperature overnight; the mixture was filtered through a pad of diatomaceous earth and volatile material was removed by evaporation to give the title compound (13 g) as a brown solid. NMR (CDCl$_3$) 1.75 (s, 3H), 4.00 (s, 1H), 4.10 (brs, 2H), 6.61 (d, 1H), 7.08 (t, 1H), 7.72 (d, 1H), 8.77 (brs, 1H); m/z: 281.

Method 9

(R)-N-[3-Nitro-2-chlorophenyl]-2-hydroxy-2-methyl-3,3,3-trifluoropropanamide

The title compound was prepared by the method of Example 6 using (R)-(+)-2-hydroxy-2-methyl-3,3,3-trifluoropropanoic acid (Method 3) and 2-chloro-3-nitroaniline (Tetrahedron, 1999, 56 (2), 165–173) except that 2,6-diphenylpyridine was used instead of 2,6-di-t-butylpyridine. NMR (CDCl$_3$) 1.77 (s, 3H), 3.58 (s, 1H), 7.44 (t, 1H), 7.63 (d, 1H), 8.66 (d, 1H), 9.27 (s, 1H); m/z 311.

EXAMPLE 46

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:
1. A compound of formula (I):

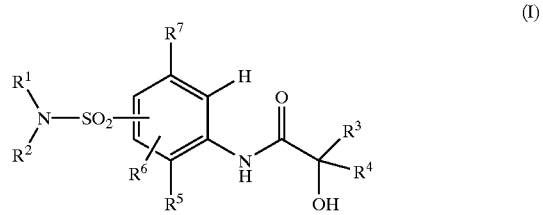

wherein:

$R^1$ and $R^2$ are each selected independently from hydrogen, phenyl optionally substituted by one or more Q, naphthyl optionally substituted by one or more Q, $C_{3-6}$cycloalkyl optionally substituted by one or more Q, $C_{2-6}$alkenyl, $C_{2-6}$alkynyl, $C_{1-6}$alkyl optionally substituted by one or more Q, $R^8T$—, $R^9C_{1-6}$alkylT— and a heterocyclic group optionally substituted on a ring carbon by one or more Q and wherein if said heterocyclic group contains an —NH— moiety that nitrogen may be optionally substituted by a group selected from D, or $R^1$ and $R^2$ together with the nitrogen atom to which they are attached form a group Het which is optionally substituted on a ring carbon by one or more Q and wherein if group Het contains an —NH— moiety that nitrogen may be optionally substituted by a group selected from D;

$R^3$ and $R^4$ are independently $C_k$alkyl optionally substituted by 1 to 2k+1 atoms selected from fluoro and chloro wherein k is 1–3;

or $R^3$ and $R^4$ together with the carbon atom to which they are attached, form a $C_m$cycloalkyl ring optionally substituted by 1 to 2m-2 fluorine atoms wherein m is 3–5;

$R^5$ is hydrogen, $C_{1-6}$alkyl, halo$C_{1-6}$alkyl, $C_{1-6}$alkoxy, halo$C_{1-6}$alkoxy, cyano, nitro, $C_{2-6}$alkenyloxy, trifluoromethylthio, halo, hydroxy, amino, N—($C_{1-6}$alkyl)amino, N—($C_{1-6}$alkyl)2amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoyl, N—($C_{1-6}$alkyl)aminosulphonyl, N—($C_{1-6}$alkyl)$_2$aminosulphonyl, carboxy, carbamoyl, N—($C_{1-6}$alkyl)carbamoyl, N—($C_{1-6}$alkyl)$_2$carbamoyl, $C_{1-6}$alkoxycarbonyl, formyl, $C_{1-6}$alkanoyl, $C_{1-6}$alkanoyloxy, $C_{2-6}$alkenyl or $C_{2-6}$alkynyl;

$R^6$ is hydrogen or Q;

$R^7$ is hydrogen, trifluoromethyl, $C_{1-4}$alkyl, halo, hydroxy, trifluoromethoxy, cyano, $C_{1-4}$alkoxy, formyl, $C_{1-4}$alkanoyl, $C_{1-4}$alkanoyloxy, amino, N—($C_{1-4}$alkyl)amino, N—($C_{1-4}$alkyl)$_2$amino, $C_{1-4}$alkanoylamino, $C_{1-4}$alkanoyl(N—$C_{1-4}$alkyl)amino, nitro, carboxy, carbamoyl, ureido, $C_{1-4}$alkoxycarbonyl, thiol, $C_{1-4}$alkylsulphanyl, $C_{1-4}$alkylsulphinyl, $C_{1-4}$alkylsulphonyl, sulphamoyl, N—($C_{1-4}$alkyl)aminosulphonyl, N—($C_{1-4}$alkyl)$_2$aminosulphonyl, N'—($C_{1-4}$alkyl)ureido or N'—($C_{1-4}$alkyl)$_2$ureido;

$R^8$ is $C_{1-6}$alkyl optionally substituted by one or more $R^{10}$, $C_{3-6}$cycloalkyl optionally substituted by one or more $R^{10}$, phenyl optionally substituted by one or more $R^{10}$, naphthyl optionally substituted by one or more $R^{10}$ or a heterocyclic group optionally substituted on a ring carbon by one or more $R^{10}$ and if said heterocyclic group contains an —NH— moiety that nitrogen may be optionally substituted by a group selected from D;

$R^9$ is phenyl optionally substituted by one or more $R^{10}$, naphthyl optionally substituted by one or more $R^{10}$ or a heterocyclic group optionally substituted on a ring carbon by one or more $R^{10}$ and if said heterocyclic group contains an —NH— moiety that nitrogen may be optionally substituted by a group selected from D;

$R^{10}$ is $C_{1-6}$alkyl-M— optionally substituted by $R^{16}$, halo, hydroxy, cyano, formyl, amino, nitro, carboxy, carbamoyl, thiol, sulphamoyl, phenyl optionally substituted by $R^{16}$, a heterocyclic group optionally substituted on a ring carbon by $R^{16}$ wherein if said heterocyclic group contains an —NH— moiety that nitrogen may be optionally substituted by a group selected from D;

Q is $C_{1-6}$alkyl-M— optionally substituted with one or more $R^{11}$, $C_{2-6}$alkenyl-M— optionally substituted by one or more $R^{11}$, $C_{2-6}$alkynyl-M— optionally substituted by one or more $R^{11}$, $R^{13}$—M—, hydroxy, halo, cyano, thiol, sulphamoyl, nitro, carboxy, amino, carbamoyl, formyl or ureido;

T is —O—, —C(O)—, —NH—, —N(N—$C_{1-6}$alkyl)-, —C(O)NH—, —NHC(O)—, —C(O)N(N—$C_{1-6}$alkyl)—, —N(N—$C_{1-6}$alkyl)C(O)—, —SO$_2$—, —C(S)—, —C(S)NH—, —NHC(S)—, —C(S)N(N—$C_{1-6}$alkyl)- or —N(N—$C_{1-6}$alkyl)C(S)—;

M is —(O—, —N($R^{14}$)—, —C(O)—, —N($R^{14}$)C(O)—, —C(O)N($R^{14}$)—, —S(O)$_n$— wherein n is 0–2, —OC(O)—, —C(O)O—, —N($R^{14}$)C(O)O—, —OC(O)N($R^{14}$), —C(S)N($R^{14}$)—, —N($R^{14}$)C(S)—, —SO$_2$N($R^{14}$)—, —N($R^{14}$)SO$_2$—, —N($R^{14}$)C(O)N($R^{14}$)—, —N($R^{14}$)C(S)N($R^{14}$)—, —SO$_2$NHC(O)—, —SO$_2$N($R^{14}$)C(O)—, —C(O)NHSO$_2$—, —C(O)N($R^{14}$)SO$_2$— or M is a direct bond;

D is $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N—($C_{1-6}$alkyl)$_2$carbamoyl, benzoyl, (heterocyclic group)carbonyl, phenylsulphonyl, (heterocyclic group)sulphonyl, phenyl or a carbon linked heterocyclic group, and wherein any $C_{1-6}$alkyl group may be optionally substituted by one or more $R^{11}$, and wherein any phenyl or heterocyclic group may be optionally substituted on a ring carbon by one or more groups selected from $R^{10}$ and if a heterocyclic group contains an —NH— moiety that nitrogen may be optionally substituted by a group selected from E;

E is $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N—($C_{1-6}$alkyl)$_2$carbamoyl, $C_{1-6}$alkoxy$C_{1-6}$alkanoyl, phenyl$C_{1-6}$alkyl, benzoyl, phenyl$C_{1-6}$alkanoyl, phenyl$C_{1-6}$alkoxycarbonyl or phenylsulphonyl.

$R^{11}$ is hydroxy, nitro, cyano, thiol, halo, ureido, amino, N—($C_{1-6}$alkyl)amino, N—($C_{1-6}$alkyl)$_2$amino, carboxy, $C_{1-6}$alkoxy, carbamoyl, N—($C_{1-6}$alkyl)carbamoyl, N—($C_{1-6}$alkyl)$_2$carbamoyl, formyl, sulphamoyl, N—$C_{1-6}$alkylaminosulphonyl, N—($C_{1-6}$alkyl)$_2$aminosulphonyl, $C_{1-6}$alkylsulphonylamino, $C_{1-6}$alkanoylamino, $C_{1-6}$alkylsulphanyl, $C_{1-6}$alkylsulphinyl, $C_{1-6}$alkylsulphonyl, phenyl optionally substituted by one or more $R^{10}$, naphthyl optionally substituted by one or more $R^{10}$, or a heterocyclic group optionally substituted on a ring carbon by one or more $R^{10}$, and if said heterocyclic group contains an —NH— moiety that nitrogen may be optionally substituted by a group selected from D;

$R^{13}$ is phenyl optionally substituted by one or more $R^{10}$, $C_{3-6}$cycloalkyl optionally substituted by one or more $R^{10}$, naphthyl optionally substituted by one or more $R^{10}$, or a heterocyclic group optionally substituted on a ring carbon by one or more $R^{10}$ and if said heterocyclic group contains an —NH— moiety that nitrogen may be optionally substituted by a group selected from D;

$R^{14}$ is hydrogen or $C_{1-6}$alkyl optionally substituted by one or more $R^{15}$ with the proviso that $R^{15}$ is not a substituent on the carbon attached to the nitrogen atom of M;

$R^{15}$ is halo, hydroxy, amino, cyano, nitro, trifluoromethyl, trifluoromethoxy, $C_{1-6}$alkyl, $C_{2-6}$alkenyl, $C_{2-6}$alkynyl, N—($C_{1-6}$alkyl)amino, N—($C_{1-6}$alkyl)$_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl (N—$C_{1-6}$alkyl)amino, thio, $C_{1-6}$alkylsulphanyl, $C_{1-6}$alkylsuphinyl, $C_{1-6}$alkylsulphonyl, sulphamoyl, N—($C_{1-6}$alkyl)aminosulphonyl, N—($C_{1-6}$alkyl)$_2$ aminosulphonyl, carboxy, carbamoyl, N—($C_{1-6}$alkyl) carbamoyl, N—($C_{1-6}$alkyl)$_2$carbamoyl, $C_{1-6}$alkoxycarbonyl, $C_{1-6}$alkanoyl or formyl;

$R^6$ is hydroxy, halo, cyano, $C_{1-6}$alkoxy, formyl, $C_{1-6}$alkanoyl, $C_{1-6}$alkanoyloxy, amino, N—($C_{1-6}$alkyl) amino, N—($C_{1-6}$alkyl)$_2$amino, $C_{1-6}$alkanoylamino, $C_{1-6}$alkanoyl(N—$C_{1-6}$alkyl)amino, carboxy, carbamoyl, $C_{1-6}$alkoxycarbonyl, $C_{1-6}$alkylsulphanyl, $C_{1-6}$alkylsulphinyl, $C_{1-6}$alkylsulphonyl, sulphamoyl, N—($C_{1-6}$alkyl)aminosulphonyl or N—($C_{1-6}$alkyl)$_2$ aminosulphonyl;

and wherein if one of $R^5$, $R^6$ and $R^7$ is hydrogen the others cannot be hydrogen;

or a pharmaceutically acceptable salt or an in vivo hydrolysable ester thereof.

2. A compound of formula (I) according to claim 1 wherein $R^1$ and $R^2$ are each selected independently from hydrogen, phenyl optionally substituted by one or more Q, $C_{3-6}$cycloalkyl optionally substituted by one or more Q, $C_{1-6}$alkyl optionally substituted by one or more Q and a heterocyclic group optionally substituted on a ring carbon by one or more Q, or $R^1$ and $R^2$ together with the nitrogen atom to which they are attached form a group Het which is optionally substituted on a ring carbon by one or more Q; wherein Q is selected from hydroxy, acetamido, acetyl, dimethylamino, methoxy or methyl;

or a pharmaceutically acceptable salt or an in vivo hydrolysable ester thereof.

3. A compound of formula (I) according to claim 1 wherein $R^1$ and $R^2$ are each selected independently from hydrogen, phenyl, 4-methylphenyl, 2-methoxyphenyl, 4-methoxyphenyl, 4-acetylphenyl, 4-acetamidophenyl, 4-dimethylaminophenyl, 2,4-dimethoxyphenyl, 3,4-dimethoxyphenyl, methyl, ethyl, isopropyl, 4-hydroxycyclohexyl, 1-methyl-2-hydroxyethyl, 1,1-dimethyl-2-hydroxyethyl, 2-hydroxyethyl, 2-hydroxypropyl, 2,3-dihydroxypropyl, pyrid-3-yl and 5-methylpyrid-2-yl, 2-methoxypyrid-5-yl, or $R^1$ and $R^2$ together with the nitrogen atom to which they are attached form 3-hydroxypyrrolidin-1-yl, 3-hydroxypiperidin-1-yl, 4-hydroxypiperidin-1-yl or morpholino;

or a pharmaceutically acceptable salt or an in vivo hydrolysable ester thereof.

4. A compound of formula (I) according to claim 1 wherein one of $R^3$ and $R^4$ is methyl and the other is trifluoromethyl;

or a pharmaceutically acceptable salt or an in vivo hydrolysable ester thereof.

5. A compound of formula (I) according to claim 1 wherein $R^5$ is selected from chloro or methoxy;

or a pharmaceutically acceptable salt or an in vivo hydrolysable ester thereof.

6. A compound of formula (I) according to claim 1 wherein $R^6$ is selected from hydrogen, chloro, iodo, methylsulphanyl or methyl;

or a pharmaceutically acceptable salt or an in vivo hydrolysable ester thereof.

7. A compound of formula (I) according to claim 1 wherein $R^7$ is hydrogen or methoxy;

or a pharmaceutically acceptable salt or an in vivo hydrolysable ester thereof.

8. A compound of formula (I) selected from:

(R)-N-[2,3-dichloro-4-(methylaminosulphonyl)phenyl]-3,3,3-trifluoro-2-hydroxy-2-methylpropanamide;

(R)-N-{2,3-dichloro-4-[(1-methyl-2-hydroxyethylamino) sulphonyl]phenyl}-3,3,3-trifluoro-2-hydroxy-2-methylpropanamide;

(R)-N-[2-chloro-3-methyl-4-((S)-2-hydroxypropylamino-sulphonyl)phenyl]-3,3,3-trifluoro-2-hydroxy-2-methylpropanamide;

(R)-N-[2-chloro-3-methyl-4-((R,S)-2-hydroxypropylaminosulphonyl)phenyl]-3,3,3-trifluoro-2-hydroxy-2-methylpropanamide;

(R)-N-{2-chloro-3-methyl-4-[(3-hydroxyprop-2-ylamino)sulphonyl]phenyl}-3,3,3-trifluoro-2-hydroxy-2-methylpropanamide;

(R)-N-[2,3-dichloro-4-((S)-3-hydroxyprop-2-ylaminosulphonyl)phenyl]-3,3,3-trifluoro-2-hydroxy-2-methylpropanamide;

(R)-N-[2-chloro-3-methyl-4-((S)-2-hydroxypropylamino-sulphonyl)phenyl]-3,3,3-trifluoro-2-hydroxy-2-methylpropanamide;

(R)-N-[2-chloro-3-methyl-4-((R)-2-hydroxypropylamiiosulphonyl)phenyl]-3,3,3-trifluoro-2-hydroxy-2-methylpropanamide;

or a pharmaceutically acceptable salt or an in vivo hydrolysable ester thereof.

9. A process for preparing a compound of formula (I) according to claim 1 or a pharmaceutically acceptable salt or an in vivo hydrolysable ester thereof, which process (in which variable groups are as defined in claim 1 for formula (I) unless otherwise stated) comprises of:

(a) deprotecting a protected compound of formula (II):

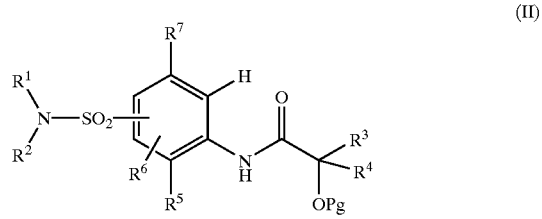

(II)

where Pg is an alcohol protecting group;

(b) coupling an aniline of formula (III):

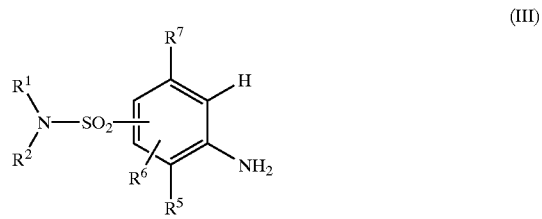

(III)

with an acid of formula (IV):

(IV)

wherein G is a hydroxyl group;

(c) coupling an aniline of formula (III) with an activated acid derivative of formula (IV) wherein G is a hydroxyl group which may be protected as an ester, ether or silyl ether;

(d) reacting a compound of formula (V):

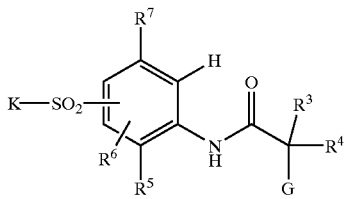

(V)

where K is a leaving atom or group and G is a hydroxyl group which may be protected as an ester; with an amine of formula (VI):

$R^1R^2NH$ (IV);

and thereafter if necessary:
   i) converting a compound of the formula (I) into another compound of the formula (I);
   ii) removing any protecting groups; or
   iii) forming a pharmaceutically acceptable salt or in vivo hydrolysable ester.

10. A pharmaceutical composition which comprises a compound of formula (I) according to any one of claims 1–8, or a pharmaceutically acceptable salt or in vivo hydrolysable ester thereof in association with a pharmaceutically-acceptable diluent or carrier.

11. A method for the treatment of a disease state associated with reduced PDH activity, said method comprising administering to a warm-blooded animal in need thereof a PDH activity-elevating amount of a compound of the formula (I) according to any one of claims 1–8, or a pharmaceutically acceptable salt or in vivo hydrolysable ester thereof.

12. The method of claim 11 wherein said disease state is selected from the group consisting of diabetes mellitus, obesity and lactic acidaemia.

13. The method of claim 11 wherein said disease state is diabetes mellitus.

\* \* \* \* \*